US010376877B2

(12) United States Patent
Schaff et al.

(10) Patent No.: US 10,376,877 B2
(45) Date of Patent: Aug. 13, 2019

(54) AUTOMATED SAMPLE PROCESSING, FLUID DISTRIBUTION, AND SEDIMENTATION ASSAY

(71) Applicant: Sandstone Diagnostics, Inc., Livermore, CA (US)

(72) Inventors: Ulrich Schaff, Livermore, CA (US); Christopher Tomkins-Tinch, Rochester, NY (US); Jason Sauers, Cupertino, CA (US); Greg Sommer, Livermore, CA (US)

(73) Assignee: Sandstone Diagnostics, Inc., Pleasanton, CA (US)

( * ) Notice: Subject to any disclaimer, the term of this patent is extended or adjusted under 35 U.S.C. 154(b) by 666 days.

(21) Appl. No.: 14/766,665

(22) PCT Filed: Feb. 6, 2014

(86) PCT No.: PCT/US2014/015170
§ 371 (c)(1),
(2) Date: Aug. 7, 2015

(87) PCT Pub. No.: WO2014/124179
PCT Pub. Date: Aug. 14, 2014

(65) Prior Publication Data
US 2016/0023204 A1    Jan. 28, 2016

Related U.S. Application Data

(60) Provisional application No. 61/761,891, filed on Feb. 7, 2013.

(51) Int. Cl.
*B01L 3/00* (2006.01)
*B04B 5/04* (2006.01)
(Continued)

(52) U.S. Cl.
CPC ........... *B01L 3/502* (2013.01); *B01F 11/0002* (2013.01); *B01F 11/0068* (2013.01);
(Continued)

(58) Field of Classification Search
None
See application file for complete search history.

(56) References Cited

U.S. PATENT DOCUMENTS 2,569,702 A  10/1951  Warner
3,401,696 A   9/1968  O'Brien
(Continued)

FOREIGN PATENT DOCUMENTS

AT    213017 T    2/2002
AU    8083891 A   12/1991
(Continued)

OTHER PUBLICATIONS

Patent Cooperation Treaty, International Search Report and Written Opinion of the International Searching Authority, International Patent Application No. PCT/US2014/015170, dated May 23, 2014, 12 Pages.
(Continued)

Primary Examiner — Jill A Warden
Assistant Examiner — Brittany I Fisher
(74) Attorney, Agent, or Firm — Fenwick & West LLP

(57) ABSTRACT

The disclosure describes methods and devices with which to process and analyze difficult chemical, biological, environmental samples including but not limited to those containing bulk solids or particulates. The disclosure includes a cartridge which contains a separation tube as well as one or more valves and cavities for receiving raw sample materials and for directing and containing various fluids or samples. The cartridge may contain a separation fluid or density medium of defined density, and structures which direct (Continued)

Side view particulates toward defined regions of the cartridge. Embodiments can include a rotational device for rotating the cartridge at defined rotational rates for defined time intervals. Embodiments allowing multiple assays from a single sample are also disclosed. In some embodiments, this device is used for direct processing and chemical analysis of food, soil, blood, stool, motor oil, semen, and other samples of interest.

26 Claims, 10 Drawing Sheets

(51) Int. Cl.
G01N 1/40 (2006.01)
B01F 11/00 (2006.01)
B01F 15/00 (2006.01)
B01F 15/02 (2006.01)
G01N 33/49 (2006.01)
B01F 13/00 (2006.01)

(52) U.S. Cl.
CPC ...... *B01F 13/0052* (2013.01); *B01F 13/0064* (2013.01); *B01F 15/00844* (2013.01); *B01F 15/0233* (2013.01); *B01L 3/50273* (2013.01); *B04B 5/0407* (2013.01); *G01N 1/4077* (2013.01); *G01N 33/491* (2013.01); *B01F 2215/0454* (2013.01); *B01L 2200/027* (2013.01); *B01L 2200/0642* (2013.01); *B01L 2200/0647* (2013.01); *B01L 2200/0668* (2013.01); *B01L 2200/0684* (2013.01); *B01L 2200/16* (2013.01); *B01L 2300/0681* (2013.01); *B01L 2300/0858* (2013.01); *B01L 2300/0864* (2013.01); *B01L 2300/0867* (2013.01); *B01L 2400/0409* (2013.01); *G01N 2001/4083* (2013.01)

(56) References Cited

U.S. PATENT DOCUMENTS

| | | | |
|---|---|---|---|
| 3,518,164 A | 6/1970 | Andelin | |
| 4,125,375 A | 11/1978 | Hunter et al. | |
| 4,156,570 A | 5/1979 | Wardlaw | |
| 4,300,404 A | 11/1981 | Mehl et al. | |
| D267,118 S | 11/1982 | Bernett | |
| 4,530,816 A | 7/1985 | Douglas-Hamilton | |
| 4,683,579 A | 7/1987 | Wardlaw | |
| 4,799,599 A | 1/1989 | Herrmann | |
| 5,061,381 A | 10/1991 | Burd | |
| 5,068,089 A | 11/1991 | Ericsson et al. | |
| 5,122,284 A | 6/1992 | Braynin et al. | |
| 5,173,193 A | 12/1992 | Schembri | |
| 5,186,844 A | 2/1993 | Burd et al. | |
| 5,232,120 A | 8/1993 | Dunken et al. | |
| 5,242,606 A | 9/1993 | Braynin et al. | |
| 5,316,952 A | 5/1994 | Brimhall | |
| 5,342,790 A | 8/1994 | Levine et al. | |
| 5,358,690 A | 10/1994 | Guirguis | |
| 5,472,603 A * | 12/1995 | Schembri | G01N 21/07 210/360.1 |
| 5,605,803 A | 2/1997 | Herr et al. | |
| 5,770,795 A | 6/1998 | Behar et al. | |
| 5,786,898 A | 7/1998 | Fitzpatrick | |
| D398,993 S | 9/1998 | Jones | |
| 5,807,360 A | 9/1998 | Shubin | |
| 5,895,749 A | 4/1999 | Alvarez | |
| 5,935,800 A | 8/1999 | Alvarez | |
| 6,153,148 A * | 11/2000 | Thomas | B01L 3/50215 422/548 |
| 6,291,178 B1 | 9/2001 | Schneider | |
| 6,319,469 B1 | 11/2001 | Mian et al. | |
| 6,458,553 B1 * | 10/2002 | Colin | B01L 3/502 435/283.1 |
| 6,491,656 B1 | 12/2002 | Morris | |
| 6,632,399 B1 * | 10/2003 | Kellogg | B01F 13/0059 422/505 |
| 6,864,046 B1 | 3/2005 | Prien | |
| 7,033,747 B2 | 4/2006 | Gordon et al. | |
| 7,077,000 B2 | 7/2006 | Gouldsworthy | |
| D529,170 S | 9/2006 | Wang | |
| 7,157,049 B2 | 1/2007 | Valencia et al. | |
| D560,813 S | 1/2008 | Matusuura | |
| 7,384,602 B2 | 6/2008 | Nagaoka et al. | |
| 7,758,810 B2 | 7/2010 | Lee et al. | |
| D631,558 S | 1/2011 | Harmston et al. | |
| 7,947,026 B2 | 5/2011 | Herr et al. | |
| D641,866 S | 7/2011 | Burgess et al. | |
| 7,993,315 B2 | 8/2011 | Matusuura | |
| 8,163,253 B1 | 4/2012 | Hartselle | |
| D660,451 S | 5/2012 | Matusuura | |
| 8,353,887 B2 | 1/2013 | Matusuura | |
| 8,475,422 B2 | 7/2013 | Wu | |
| 8,535,622 B2 | 9/2013 | Shany et al. | |
| 8,945,914 B1 | 2/2015 | Schaff et al. | |
| 8,962,346 B2 | 2/2015 | Schaff et al. | |
| D739,552 S | 9/2015 | Hoke | |
| 9,304,129 B2 | 4/2016 | Schaff et al. | |
| D762,299 S | 7/2016 | Matusuura | |
| 9,594,034 B1 | 3/2017 | Pompa | |
| 2002/0151040 A1 | 10/2002 | O' Keefe et al. | |
| 2002/0151043 A1 | 10/2002 | Gordon | |
| 2003/0127609 A1 | 7/2003 | El-Hage et al. | |
| 2005/0011261 A1 | 1/2005 | Lyon | |
| 2005/0059163 A1 | 3/2005 | Dastane | |
| 2006/0068490 A1 | 3/2006 | Tang et al. | |
| 2007/0031895 A1 | 2/2007 | Herr et al. | |
| 2007/0224591 A1 * | 9/2007 | Gui | B01L 3/502746 435/4 |
| 2007/0286774 A1 | 12/2007 | Barholm-Hansen et al. | |
| 2008/0202217 A1 * | 8/2008 | Larsen | G01N 15/12 73/61.41 |
| 2009/0148869 A1 | 6/2009 | Zaugg et al. | |
| 2009/0263848 A1 | 10/2009 | Obermann et al. | |
| 2010/0240142 A1 | 9/2010 | Saiki et al. | |
| 2011/0084070 A1 | 4/2011 | Martheenal | |
| 2011/0086378 A1 | 4/2011 | Shany et al. | |
| 2011/0111981 A1 * | 5/2011 | Love | C12Q 1/703 506/10 |
| 2011/0206646 A1 * | 8/2011 | Alfonso | A61K 35/28 424/93.7 |
| 2012/0052485 A1 | 3/2012 | Shany et al. | |
| 2012/0065047 A1 * | 3/2012 | Chapman | B01L 3/5021 494/16 |
| 2012/0164751 A1 | 6/2012 | Liang et al. | |
| 2012/0234731 A1 * | 9/2012 | Senftleber | B03C 1/288 209/39 |
| 2012/0282707 A1 * | 11/2012 | Borch | B01L 3/502738 436/177 |
| 2013/0236376 A1 | 9/2013 | Augstein et al. | |
| 2016/0023204 A1 | 1/2016 | Schaff et al. | |
| 2016/0047794 A1 | 2/2016 | Saiki | |
| 2016/0320276 A9 | 11/2016 | Schaff et al. | |
| 2017/0056878 A1 | 3/2017 | Peytavi et al. | |

FOREIGN PATENT DOCUMENTS

| | | |
|---|---|---|
| AU | 2925592 A | 6/1993 |
| AU | 5427699 A | 3/2000 |
| AU | 774508 B2 | 7/2004 |
| CA | 2346974 A1 | 12/1991 |
| CA | 2346975 A1 | 12/1991 |
| CA | 2347669 A1 | 12/1991 |
| CA | 2120244 A1 | 5/1993 |
| CA | 2343010 A1 | 3/2000 |
| CA | 2082827 C1 | 10/2001 |
| CN | 101802622 A | 8/2010 |
| CN | 103487596 A | 1/2014 |
| CN | 103499702 A | 1/2014 |
| DE | 69130986 T2 | 9/1999 |

(56) References Cited

FOREIGN PATENT DOCUMENTS

| | | |
|---|---|---|
| DE | 6990870 T2 | 11/2002 |
| EP | 0106536 | 4/1984 |
| EP | 0173811 A1 | 3/1986 |
| EP | 0532591 A1 | 3/1993 |
| EP | 0608006 A2 | 7/1994 |
| EP | 0611323 A1 | 8/1994 |
| EP | 965388 A2 | 12/1999 |
| EP | 0965388 A2 | 12/1999 |
| EP | 1105457 A1 | 6/2001 |
| EP | 2072131 A1 | 6/2009 |
| EP | 2219034 A1 | 8/2010 |
| FR | 2782729 A1 | 3/2000 |
| GB | 2162312 A | 1/1986 |
| JP | S59-073766 A | 4/1984 |
| JP | H07-500910 A | 1/1995 |
| JP | 3256542 B2 | 2/2002 |
| JP | 2002-523083 A | 7/2002 |
| JP | 2006/505766 A | 2/2006 |
| JP | 2009-150733 A | 7/2009 |
| JP | 2009-150880 A | 7/2009 |
| JP | 2009-233532 A | 10/2009 |
| JP | 2009-300433 A | 12/2009 |
| JP | 2013/513794 A | 4/2013 |
| JP | 2013/541013 A | 11/2013 |
| JP | 5-508709 B2 | 6/2014 |
| JP | 2014/518374 A | 7/2014 |
| WO | WO 91/018656 A1 | 12/1991 |
| WO | WO 93/008893 A1 | 5/1993 |
| WO | WO 94/26299 | 11/1994 |
| WO | WO 2000/012674 A1 | 3/2000 |
| WO | WO 2009/060617 A1 | 5/2009 |
| WO | WO 2011/110469 A1 | 9/2011 |
| WO | WO 2011/137906 A1 | 11/2011 |
| WO | WO 2012/026970 A2 | 3/2012 |
| WO | WO 2012/055707 A1 | 5/2012 |
| WO | WO 2012/164552 A1 | 12/2012 |
| WO | WO 2014/191207 A1 | 12/2014 |
| WO | WO 2015/172255 A1 | 11/2015 |
| WO | WO 2016/188430 A1 | 12/2016 |

OTHER PUBLICATIONS

Baldwin, R. L., "How Hofmeister Ion Interactions Affect Protein Stability," Biophysical Journal, Oct. 1996, pp. 2056-2063, vol. 71.
Carney, J., "Rapid Diagnostic Tests Employing Latex Particles," Analytical Proceedings, Apr. 1990, pp. 99-100, vol. 27.
Czeiger, D. et al., "Measurement of Circulating Cell-Free DNA Levels by a New Simple Fluorescent Test in Patients With Primary Colorectal Cancer," Am J Clin Pathol, 2011, pp. 264-270, vol. 135.
Goldshtein, H. et al., "A Rapid Direct Fluorescent Assay for Cell-Free DNA Quantification in Biological Fluids", Annals of Clinical Biochemistry, 2009, pp. 488-494, vol. 46.
Lim, C. T. et al., "Bead-Based Microfluidic Immunoassays: The Next Generation," Biosensors and Bioelectronics, 2007, pp. 1197-1204, vol. 22.
Lo, Y. M. D. et al., "Plasma DNA Ax A Prognostic Marker in Trauma Patients," Clinical Chemistry, 2000, pp. 319-323, vol. 46, No. 3.
Maes, M. L. et al., "Comparison of Sample Fixation and the Use of LDS-751 or Anti-CD45 for Leukocyte Identification in Mouse Whole Blood for Flow Cytometry," Journal of Immunological Methods, Jan. 30, 2007, pp. 79-86, vol. 319, No. 1-2.
Price, C. P. et al., "Light-Scattering Immunoassay", Principles and Practice of Immunoassay (Second Edition); Chapter 18, 1997, pp. 446-447.
Rhodes, A. et al., "Plasma DNA Concentration as a Predictor of Mortality and Sepsis in Critically Ill Patients," Critical Care, 2006, pp. 1-7, vol. 10, No. 2.
Rider, T. H. et al., "A B Cell-Based Sensor for Rapid Identification of Pathogens," www.sciencemag.org, Science, Jul. 11, 2003, pp. 213-215, vol. 301.
Schaff, U. Y. et al., "Whole Blood Immunoassay Based on Centrifugal Bead Sedimentation," Clinical Chemistry, 2011, pp. 753-761, vol. 57, No. 5.
Zhang, L. et al., "A New Biodosimetric Method: Branched DNA-Based Quantitative Detection of B1 DNA in Mouse Plasma," The British Journal of Radiology, Aug. 2010, pp. 694-701, vol. 83.
European Extended Search Report, European Application No. 14749441.3, dated Oct. 7, 2016, 10 pages.
Australian First Examination Report, Australian Application No. 2014214886, dated Apr. 7, 2017, 3 pages.
United States Office Action, U.S. Appl. No. 13/423,008.
Abi-Samra, K. et al., "Infrared Controlled Waxes for Liquid Handling and Storage on a CD-Microfluidic Platform", The Royal Society of Chemistry; Lab Chip, 2010, pp. 723-726.
Arlington, S.A., "Alternative-site Diagnostic Testing," Analytical Proceedings, Apr. 1990, pp. 97-101, vol. 27.
Boyko, M. et al., "Cell-Free DNA—A Marker to Predict Ischemic Brain Damage in a Rat Stroke Experimental Model", J Neurosurg Anesthesiol, Jul. 2011, pp. 222-228, vol. 23, No. 3.
Curtis, R. A. et al., "A Molecular Approach to Bioseparations: Proteinprotein and Protein-Salt Interactions", Chemical Engineering Science, 2006, pp. 907-923, vol. 61.
European Extended Search Report, European Application No. 13853032.4, dated Jun. 10, 2016, 9 pages.
Glorikian, H. et al., "Smart-Consumables Product Development Strategy: Implications for Molecular Diagnostics", DX Directions, Spring 2010, pp. 12-16.
Holmes, D. et al., "Leukocyte Analysis and Differentiation Using High Speed Microfluidic Single Cell Impedance Cytometry", Lab on a Chip, Oct. 21, 2009, pp. 2881-2889, vol. 9, No. 20.
Japanese Office Action, Japanese Application No. 2015-540917, dated Sep. 19, 2017, 4 pages (with concise explanation of relevance).
Japanese Office Action, Japanese Application No. 2015-557080, dated Jan. 9, 2018, 18 pages.
Lee, B. S. et al., "A Fully Automated Immunoassay From Whole Blood on a Disc", Lab on a Chip, Mar. 5, 2009, pp. 1548-1555, vol. 9.
Madou, M. et al., "Lab on a CD", Annual Rev. Biomed. Eng., 2006, pp. 601-628, vol. 8.
Min, J. et al., "Functional Integration of DNA Purification and Concentration Into a Real Time Micro-PCR Chip", The Royal Society of Chemistry; Lab on a Chip, 2011, pp. 259-265, vol. 11.
Patent Cooperation Treaty, International Search Report and Written Opinion of the International Searching Authority, International Patent Application No. PCT/US2013/068991, dated Feb. 5, 2014, 13 Pages.
Riegger, L. et al., "Read-Out Concepts for Multiplexed Bead-Based Fluorescence Immunoassays on Centrifugal Microfluidic Platforms", Sensors and Actuators, 2006, pp. 455-462, vol. 126.
Ziegler, A. et al., "Circulating DNA: A New Diagnostic Gold Mine?" Cancer Treatment Reviews, 2002, pp. 255-271, vol. 28.
PCT International Search Report and Written Opinion, PCT Application No. PCT/US17/33710 ISR/WO, dated Aug. 24, 2017, 11 pages.
PCT International Search Report and Written Opinion, PCT Application No. PCT/US17/21571 ISR/WO, dated Jun. 5, 2017, 17 pages.
Japanese Office Action, Japanese Application No. 2015-540917, dated Apr. 24, 2018, 9 pages (with machine translation).
https://trakfertility.com/ (Year: 2013).
https ://trakfertility.com/products/trak-male-fertility-testing-system (Year: 2017).

* cited by examiner

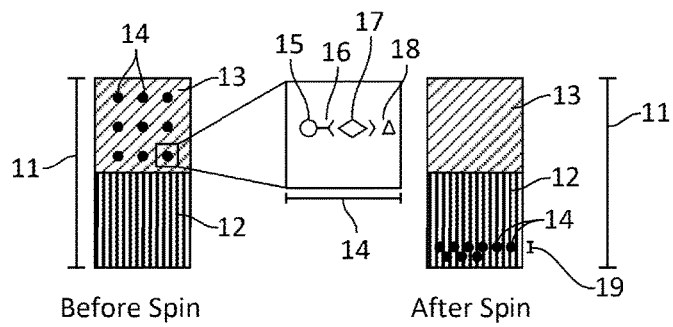
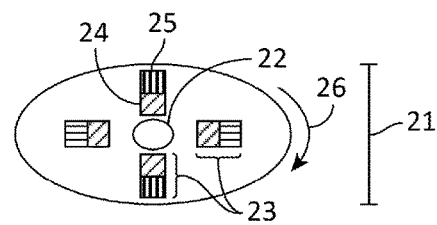
FIG. 1
FIG. 2
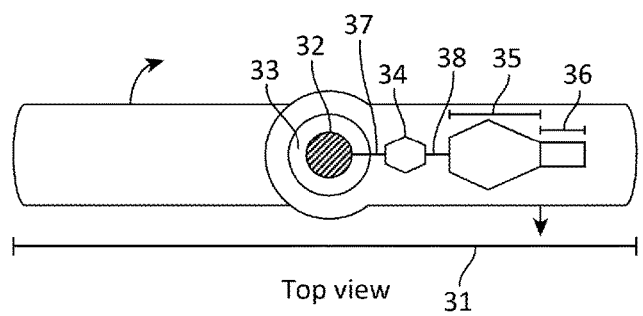
FIG. 3
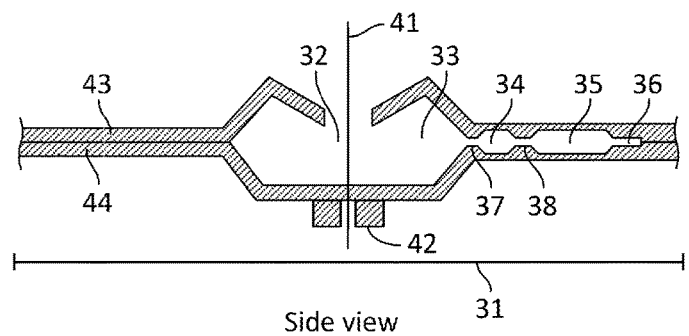
FIG. 4

A
Side view
No rotation

B
Side view
rotation

C
Side view
end of rotation

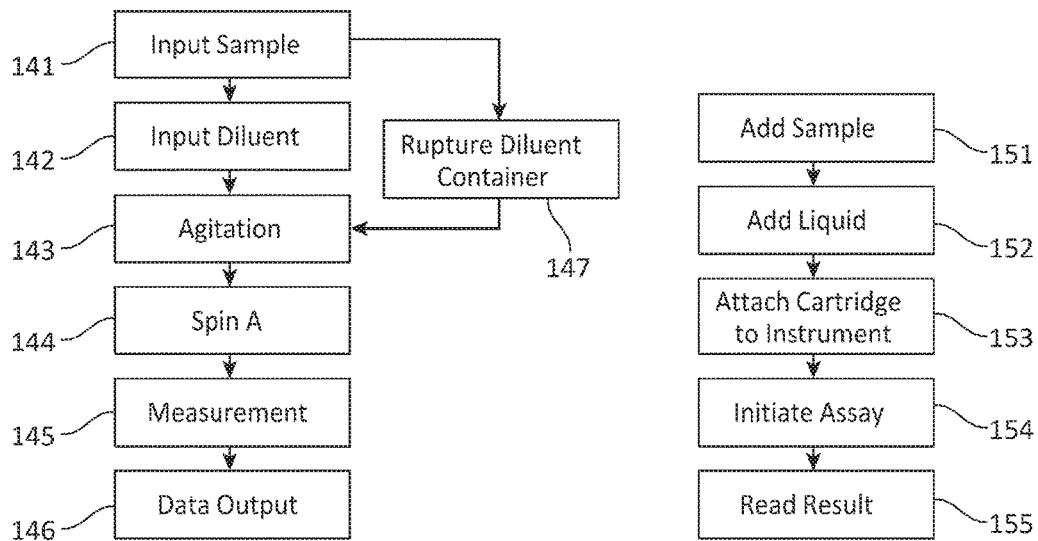
FIG. 14
FIG. 15
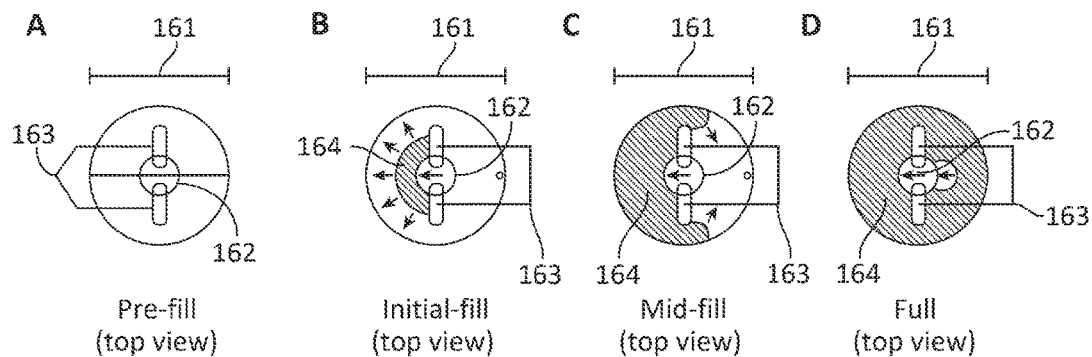
FIG. 16
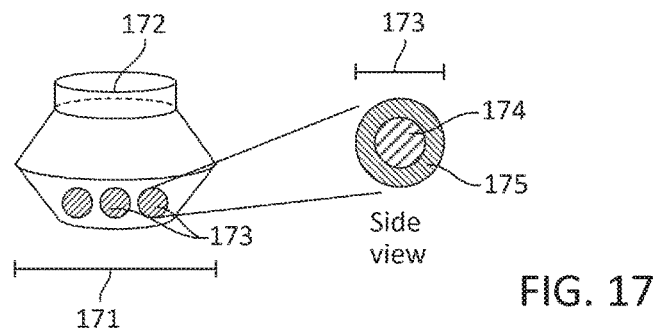
FIG. 17

AUTOMATED SAMPLE PROCESSING, FLUID DISTRIBUTION, AND SEDIMENTATION ASSAY

CROSS REFERENCE TO RELATED APPLICATIONS

This application is a 35 U.S.C. 371 national stage filing of International Application No. PCT/US2014/015170, filed on Feb. 6, 2014, which claims the benefit of U.S. Provisional Application No. 61/761,891, filed Feb. 7, 2013, each of which is incorporated by reference in its entirety.

BACKGROUND

This disclosure relates generally to fluidic processing of samples for diagnostic purposes, sedimentation or centrifugal pelleting of suspended particulate matter, and quantifying analytes by addressing pelleted fractions of the sample. More specifically, this disclosure relates to direct processing and chemical analysis of raw biological samples, including analysis of food, soil, blood, stool, semen or other samples comprising solids or particulate matter.

A wide variety of techniques including immunoassay, nucleic acid hybridization, and enzymatic color change assays are used to chemically analyze samples of interest. To produce accurate and reproducible measurements, most assays employed for chemical analysis require specific environmental and chemical conditions. For instance, a precise temperature, precise concentration of reactants, a narrow range of salt concentrations, and an absence of interfering particulates or incidental chemicals may be necessary. Because a sample to be analyzed often does not meet these exacting specifications, laborious sample preparation may be necessary. These extra sample preparation procedures may increase labor costs and time delays associated with analysis.

One class of samples which causes particular problems in automated analysis are samples comprising solids, suspended particulate matter in liquid, and/or viscous liquids. Such samples include food, soil, blood, stool, motor oil, and semen. Conventional methods for preparing such samples for chemical analysis include pulverization of solids in the presence of a carrier liquid and centrifugation to remove suspended particles from a fluid for analysis.

A wide range of prior art surrounds the concept of integrating sample preparation into an automated chemical assay by way of a disk, cartridge or capillary tube which is spun to direct various reagent fluids and separate particulates from a sample of interest. One conventional method is the sedimentation assay in which suspended beads are used to bind an analyte of interest in the sample. The suspended beads and analyte are then sedimented through a density medium by centrifugation causing the particles to be separated from the sample. Conventional sedimentation assays were initially developed for radioimmunoassays where separation and shielding of the analyte from the rest of the unprocessed sample is necessary. Conventional sedimentation assays are capable of rapidly analyzing samples with minimum system complexity but are not well suited to processing samples with intrinsic heterogeneity or samples which comprise bulk solids.

SUMMARY

The disclosure describes methods and devices with which to process and analyze chemical, biological, and environmental samples including but not limited to those containing bulk solids or particulates. The disclosure includes a cartridge which contains a separation column as well as one or more channels and cavities for receiving raw sample materials and for directing and containing various fluids. The cartridge may contain a separation fluid of defined density, and structures configured to direct sedimented particulates toward defined regions of the cartridge. Embodiments can include a rotational device for rotating the cartridge at defined rotational rates for defined time intervals. Embodiments allowing multiple assays from a single sample are also disclosed. In some embodiments, the disclosed methods and devices are used for direct processing and chemical analysis of food, soil, blood, stool, motor oil, semen, and other samples of interest.

BRIEF DESCRIPTION OF THE FIGURES

The accompanying drawings illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 1 shows a sedimentation assay chamber before and after spinning, in accordance with one embodiment.

FIG. 2 shows a sedimentation assay chamber oriented on a disk, in accordance with one embodiment.

FIG. 3 shows a top view of an exemplary sedimentation assay cartridge comprising a sample inlet cavity, a mixing chamber and a separation tube, in accordance with one embodiment.

FIG. 4 shows a side view of the exemplary sedimentation assay cartridge shown in FIG. 3, in accordance with one embodiment.

FIG. 14 depicts a step-wise process diagram for analysis of solid samples, in accordance with one embodiment.

FIG. 15 depicts a step-wise process diagram for analysis of solid samples from the user perspective, in accordance with one embodiment.

FIGS. 16A-16D illustrate fluid flow in a sample inlet cavity with self-venting before (FIG. 16A), during (FIGS. 16B and 16C) and after (FIG. 16D) filling the cavity, in accordance with one embodiment.

FIG. 17 shows a sample inlet cavity comprising several reagent-coated agitation beads and a cross section of a typical reagent coated agitation bead, in accordance with one embodiment.

DETAILED DESCRIPTION OF EMBODIMENTS OF THE INVENTION

Figure 5:
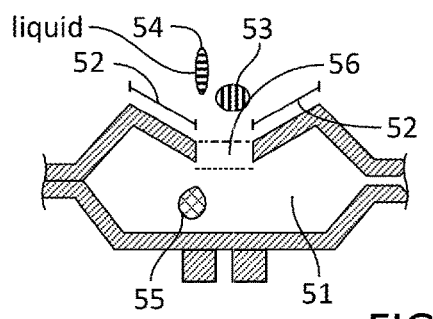
FIG. 5 shows a side view cross sectional of a first example of a sample inlet cavity, in accordance with one embodiment.

The disclosure describes devices, methods, and systems for analyzing solid or liquid samples. Particular applications for which this disclosure can be applied include diagnostic analysis of blood for proteins, nucleic acids, or cells of interest, diagnostic analysis of stool for toxins or pathogens of interest, measurement of sperm concentration and motility in semen, detection of pathogens in food, detection of allergen proteins in food, measurement of nutrient compounds in soil, and other suitable diagnostic and analytical applications. In some embodiments, the disclosure includes variations of a sedimentation assay technique in which beads bound to a substance of interest are sedimented through a density medium by way of centrifugal force or natural gravity. Some embodiments comprise a kit including a cartridge containing fluidic cavities for sedimentation of particles, a motorized instrument for spinning the cartridge to induce centrifugal force, optical sensors to provide a readout, or any combination thereof. In some embodiments, the cartridge is a disposable cartridge, and the user can use a new cartridge for each sample. The cartridge is designed to hold larger volumes of samples than conventional techniques. For example, the cartridge is designed for volumes of samples that are greater than 10 microliters, and some embodiments of the cartridge can hold volumes of samples of 20-200 microliters or up to a milliliter, or possibly more. The cartridge is also designed to be easily manufacturable.

FIG. 1 illustrates the principle behind various aspects of a sedimentation assay, in accordance with an embodiment. A fluidic chamber 11 contains a sample 13 which is layered atop a density medium 12. The sample may be mixed with beads 15 that are coated with a reagent 16 where the beads 15 can bind to a substance 17 of interest. The sample may be further mixed with a second reagent 18 which also binds to the substance 17 of interest and may contain a label to enhance detection. The combination of the beads, binding reagents, and substance of interest is termed a complex 14. The density medium 12 is selected such that density of the density medium 12 is higher than density of the sample 13 but lower than density of the complexes 14. The sample therefore contains suspended complexes 14 before centrifugation. Following centrifugation the complexes sediment through the density medium 12 and form a distinct layer 19 within the density medium 12. The density medium 12 may comprise a salt-solution containing heavy salts such as cesium chloride or sodium metatungstate, long chain polymers such as dextran, nanoparticles as found in Percoll, or other compounds which increase the density of water when dispersed or dissolved. The density medium may also contain detergents such as Tween 20 or emulsifiers such as soy lecithin configured to enhance the washing action as assay particles sediment through the density medium. If the density medium 12 is of uniform density, the layer 19 may be located at the bottom of the fluidic chamber 11 and be called a "pellet."

FIG. 2 illustrates a typical embodiment of a sedimentation assay. A disc 21 with a hole 22 in the center contains cavities that act as sedimentation columns 23. Each sedimentation column 23 contains a sample 24 layered on top of a density medium 25. The disk 21 is rotated in a single direction 26 and the sedimentation assay is completed in each of the sedimentation columns 23 in the manner shown in FIG. 1 "after spin." The disc may be between about 50 mm to 160 mm in diameter or any size compatible with available centrifuge equipment.

One embodiment of the cartridge is shown in FIGS. 3 and 4. The cartridge 31 comprises a polymer or another material comprising similar properties with a polymer and may be fabricated to contain a sample inlet hole 32 and a sample inlet cavity 33 to receive a sample of liquid, solid, or any combination thereof. The sample inlet cavity 33 can also be known as a receiving cavity in any of the embodiments disclosed herein. The sample inlet cavity 33 may be in fluid communication with a mixing chamber 34 by way of a narrow passage or valve 37. The valve 37 restricts fluid movement until a threshold rotation rate is passed or another condition is met. The mixing chamber 34 may be coated with reagents or contain a dose of dried or liquid reagents. Reagents may comprise assay particles and labeling agents conjugated to agents that bind to substance of interest in the sample or other suitable and appropriate reagents. The reagents may also comprise DNA dyes. Dried reagents may include reagents dried by freeze drying. The mixing chamber may further be in fluid communication with a sedimentation tube 35 by way of a second narrow passage or valve 38. The separation tube may be extended by a narrow channel 36. The narrow channel 36 provides a stable location for pelleting assay particles during sedimentation assays. The sedimentation tube 35, narrow channel 36 and the narrow channels in following figures comprise a depth or diameter such that fluid wetting and surface tension forces prevent movement of fluid through the channels unless a threshold force is applied which is caused in this case by the rotation rate of cartridge 31. The threshold force can be specified and increases as the diameter or depth of the narrow channel decreases. The cartridge may comprise a top 43 and a bottom 44 which may be produced by injection molding, embossing, machining, vacuum forming, blow molding, or other suitable polymer fabrication techniques. The top 43 and bottom 44 may be joined together by a welding or adhesion process such as ultrasonic welding, adhesives, thermal welding, or other suitable welding processes. The cartridge 31 is rotated about an axis 41 to facilitate sedimentation assays and fluid transfer steps by way of an appropriate motor securely attached to the motor adaptor feature 42 on the bottom of the cartridge. The sample inlet cavity 33 may be centered on the axis 41. The cartridge 31 can be rotated at any rate in the range of 100-15000 RPM and may be rotated clockwise or counterclockwise during processing steps. In some embodiments, additional rotations can be performed for additional time periods and can be true for any embodiments described herein.

A schematic of an example of one configuration of a sample inlet cavity 51 is shown in FIG. 5, in accordance with one embodiment. This schematic can be used with any of the cartridge embodiments described throughout. The sample inlet hole 56 is surrounded by a slanted region 52 which acts as a funnel to encourage liquid 54 and/or solid 53 samples or reagents to be added to the inlet cavity easily by a user. In some embodiments, a liquid sample may be contained within a fleece or narrow bore capillary tube which can be added to the sample inlet cavity 51 by a user. The liquid sample contained within such a capillary tube or fleece is extracted when the rotation rate of the cartridge is above a threshold rotation rate sufficient to overcome the capillary forces holding the liquid sample within the capillary tube. The sample inlet cavity 51 may also contain a pellet 55 of dried or liquid reagents to facilitate an assay.

Figure 6:
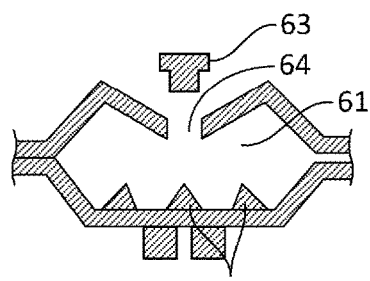
FIG. 6 shows a side view cross sectional of a second example of a sample inlet cavity having agitation enhancements, in accordance with one embodiment.

A schematic of an example of a second configuration of a sample inlet cavity 61 is shown in FIG. 6, in accordance with one embodiment, and can be used to process samples that require agitation to homogenize liquids or agitation to break up solids or solid clumps. As described previously, the sample inlet hole 64 may be surrounded by a slanted region. A lid 63 may be placed in the sample inlet hole 64 to prevent spillage of excess sample during rotation of the cartridge. The lid 63 can be a press-fit lid and may comprise a flexible polymer of a similar diameter to the sample inlet hole 64, a pressure sensitive adhesive, an adhesive foil, a threaded shaft, or any combination thereof. The sample inlet cavity may further have agitation assistance teeth 62 projecting from the top or bottom surface of the sample inlet cavity. The teeth are also known as projections herein. This configuration may be combined with any of the features of the sample inlet cavity described in FIG. 5.

Figure 7:
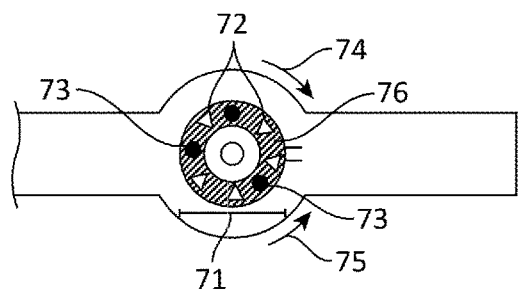
FIG. 7 illustrates a top view of one exemplary method of solid-liquid sample agitation in an assay cartridge, in accordance with one embodiment.

A cartridge incorporating a sample inlet cavity 71, as described in FIG. 6, is shown in FIG. 7, in accordance with one embodiment. The sample inlet cavity contains agitation assistance teeth 72 which may project from the top surface, bottom surface, or any combination thereof of the cavity. The sample inlet cavity contains a sample comprising a liquid 76 and solid clumps 73 which should be stirred in the liquid or broken up for proper analysis. When the cartridge is alternately rotated in a first direction 74 and then a second direction 75 the solid clumps 73 may collide with the teeth 72. These collisions may facilitate breakup of the solid clumps 73 and cause the liquid 76 to become more homogenized. The cartridge may incorporate other sedimentation assay features as described in FIGS. 3 and 4. The frequency with which the cartridge alternates between rotation in a first direction 74 and a second direction 75 can be anywhere from once per minute to 100 times per second or more.

Figure 21:
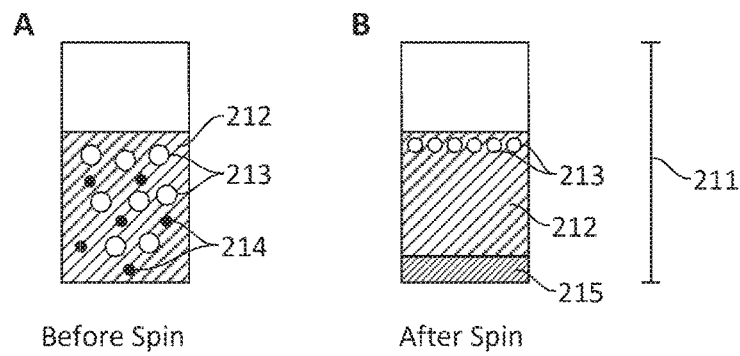
FIGS. 21A and 21B illustrate a method for denoting the top surface of liquid levels during sedimentation assays using low density particles, in accordance with one embodiment.

For all sample inlet cavities described herein, the breakup of solid clumps and solublization of compounds of interest into the fluid phase may be enhanced by the addition of compounds such as Tween 20, Pluronic 127, soy lecithin, or other detergents or emulsifiers dried in the inlet cavity or added to the sample as a solid or liquid. Compounds configured to adjust the pH or ionic strength of the sample may be included in the inlet cavity 33, 51, 61 or 71 to further aid in extraction of desired compounds, break down interfering compounds, or to enhance assay reactions. Enzymes may be included in the inlet cavity to break down interfering compounds. Agglutinating chemicals such as aluminum sulfate or chitosan may be added to the inlet cavity to cause interfering particles to clump together and be removed by filtering fluidics as described further in FIG. 21.

Figure 8:
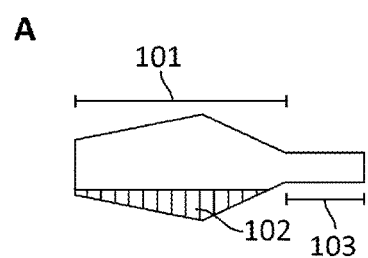
FIG. 8 shows a top view of a separation tube having angled walls, in accordance with one embodiment.
Figure 8:
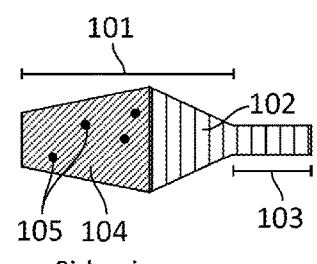
Figure 8:
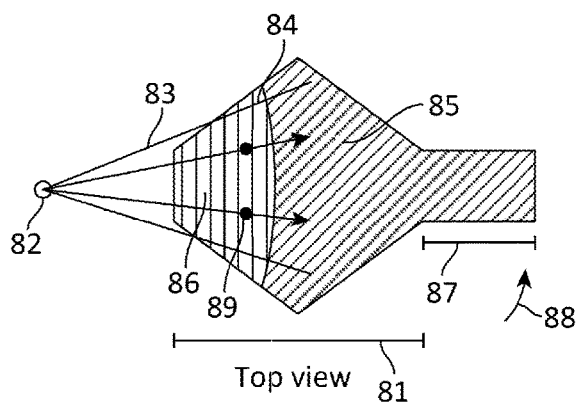
Figure 10:
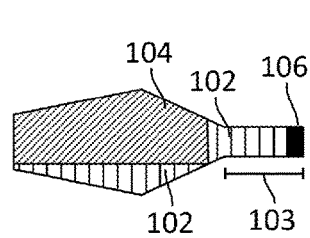
FIGS. 10A-10C shows cross-sectional side views of storage of fluid within a separation tube before rotation (FIG. 10A), after initiating rotation (FIG. 10B) and capillary stabilization of fluid layers at the end of rotation (FIG. 10C), in accordance with one embodiment.
Figure 9:
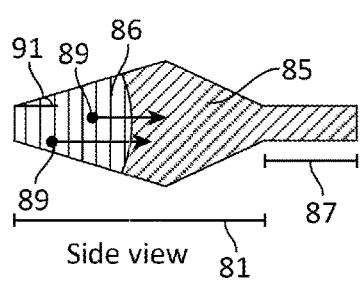
FIG. 9 shows a side view of the separation tube with angled walls, in accordance with one embodiment.

A schematic of a sedimentation tube 81 is illustrated in FIGS. 8 and 9, in accordance with one embodiment. This may be used with any of the cartridge embodiments described throughout. The sedimentation tube is configured to minimize collisions between assay particles 89 and the walls of the sedimentation tube in the region where the sample fluid 86 interfaces with the density medium 85 upon steady rotation in one direction 88. Such collisions may decrease the sensitivity of the sedimentation assay by preventing adequate washing of assay particles by trapping non-specific label between assay particles and thereby increasing background noise. Therefore, the walls of the sedimentation tube are slanted at an angle 84 that is not parallel to any radial projection line 83 from the center of rotation 82 of the cartridge. The radial projection line 83 may intersect with a wall of the sedimentation tube as shown forming the angle 84 with the wall. For example, the walls can be slanted outward, as shown in FIG. 8. The angle and the slanted walls are configured to prevent collisions between the particles and the walls of the sedimentation tube even in the event of modest misalignment of the cartridge with its center of rotation (wobble) or during acceleration and deceleration during rotation. The cartridge may further contain a narrow channel 87 to focus a pellet formed during a sedimentation assay. In addition to the angling of the side walls, the top and bottom walls of the sedimentation tube may be angled outward from parallel 91 to radial projection lines 83 from the center of rotation 82 of the cartridge to prevent collisions between these walls and the sedimentation particles 89 caused by wobble in the cartridge rotation or other suitable interactions. The narrow channel 87 may terminate in a circular region (not shown) which would collect the pellet. The circular region provides a defined area in which a pellet of assay particles can become compacted for analysis. This circular region may allow any optical signal from the pellet to be treated as a point source with ensuing advantages in optics and processing design. For example, light emitted from a circular pellet, which comprises a surface area smaller than a photodetector, may be efficiently focused with a lens onto the photodetector to facilitate analysis similar to light emitted from a point source. The sedimentation tube 81 may also have a circular or ovular cross-section that angle outward from parallel 91 to radial projection lines 83 from the center of rotation 82 of the cartridge rather than having distinct segmented sidewalls. A circular or ovular cross-section of the sedimentation tube can allow fabrication of the tube from one injection molded or blow molded piece rather than from two welded pieces of polymer. The lack of corners can increase efficiency of pelleting particles 89 into the pellet 106 (FIG. 10C) for analysis, decreasing the amount of particles left behind on the surface of the sedimentation tube 81.

FIGS. 10A-10C show cross-sectional side views of fluidic orientations in a sedimentation tube 101 while processing a sedimentation assay using one or more of any of the cartridge embodiments described herein, in accordance with one embodiment. Prior to rotation (FIG. 10A), the density medium 102 can be at the bottom of the sedimentation tube 101 or stored in a vapor-tight container in a position within the tube that does not interfere with particle sedimentation. When a sample 104 containing assay particles 105 is introduced into the sedimentation tube 101 and the cartridge is initially rotated (FIG. 10B) the sample 104 becomes layered on top of the density medium 102 oriented outward from the center of rotation of the cartridge. As the rotation continues (i.e. the cartridge can be rotated for 30 seconds-30 minutes at a rate of 100-15000 RPM) the particles sediment through the density medium and form a pellet 106 at a distal end of a narrow channel 103 of sedimentation tube 101. When the rotation is stopped (FIG. 10C), a portion of the density medium 102 can become re-oriented toward the bottom of the sedimentation tube. A portion of the density medium is trapped in the narrow channel 103 preventing contamination of the pellet 106 with unfiltered sample 104. For example, the portion is trapped by capillary action. This embodiment combines layer stability induced by the narrow region 103 with the ability to store relatively large amounts of density medium in the tube. Several microliters of fluid evaporate per year using current polymer fluid storage technologies. Containing at least tens of microliters of fluid allows for practical long term storage in an integrated analysis cartridge. The disclosed sedimentation assay approach allows for combination of large fluid storage capacity of large tubes with layer stabilizing characteristic of small tubes or channels. For example, the small tubes or channels have a thickness of less than 300 microns.

Figure 11:
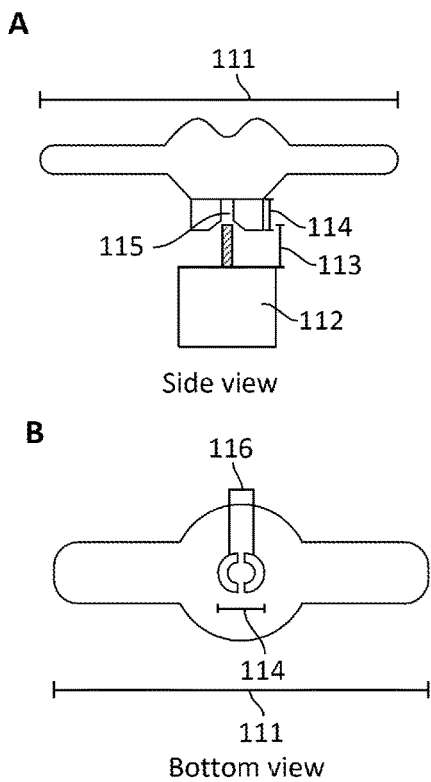
FIG. 11A-11B depict a bottom view (FIG. 11A) and a side view (FIG. 11B) of a cartridge-to-motor assembly with an adaptor integrated into the cartridge for connecting the cartridge to the motor, in accordance with one embodiment.

An example of a method for attaching an analysis cartridge or a cartridge 111 to a motor 112 is shown in FIGS. 11A-11B, in accordance with one embodiment. This method may be used with any of the cartridge embodiments described throughout. FIG. 11A shows an adaptor 114 that interfaces with the motor shaft 113 and is fabricated directly into the cartridge. The adaptor 114 may have a hole 115 through the center, wherein the hole 115 has a diameter configured such that the diameter of the motor shaft 113 fits into the diameter of the hole 115. Furthermore the hole 115 may have a conical entrance region at the center of the bottom configured to assist in directing the motor shaft into the hole 115 to achieve a pressed friction fit. An enhanced friction fit may be achieved by splitting the adaptor 114 into a plurality of blades 116 with a hole 115 in the center of the blades as shown in FIG. 11B. The material of these independent blades may be a polymer and allow the blades to elastically deform outward upon insertion of a motor shaft. The structure of the plurality of blades and the elastic deformation are configured to produce inward directed forces and increase the friction force between the adaptor 114 and the motor shaft 113, creating a secure connection which allows the motor to rotate the cartridge without slippage between the adaptor 114 and motor shaft 113. The cartridge 111 may contain any of the features shown in FIGS. 3-10.

Figure 12:
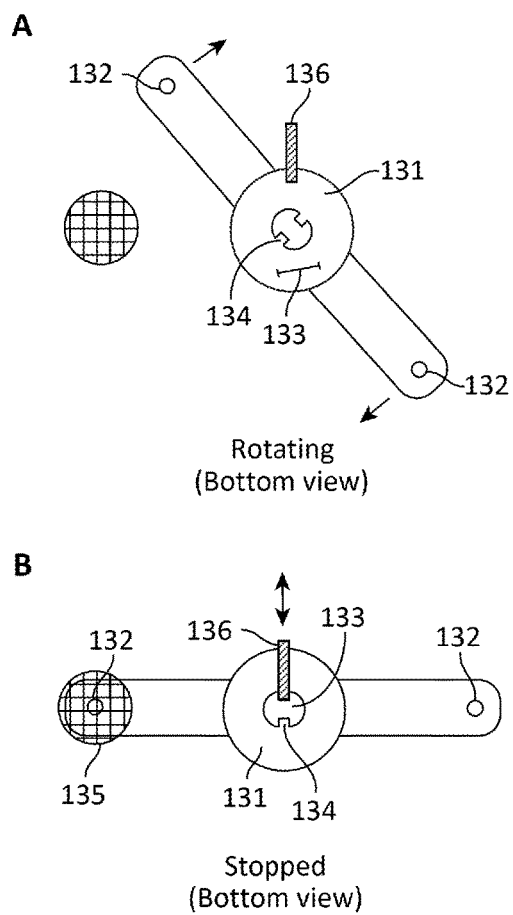
FIG. 12 illustrates a schematic of cartridge and reader instrument assembly, in accordance with one embodiment.
Figure 12:
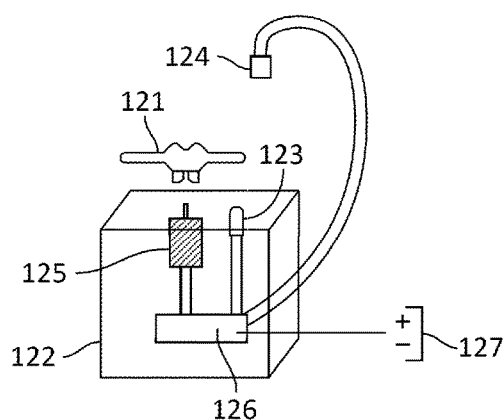

FIG. 12 shows the basic components of an instrument to spin and optically address an analysis cartridge or cartridge 121 of the type described in this disclosure, in accordance with one embodiment. The basic components shown in FIG. 12 may be used with any of the cartridge embodiments described throughout. The instrument comprises a housing 122 which can contain a light source 123 and optical sensor 124. The optical sensor 124 may be associated with additional lenses, filters and other suitable optical components. The housing can further contain a motor 125 which may be a brushed DC, a brushless DC, an AC, a servo, a stepper or any other suitable equivalent electrically driven motor. The motor 125 may also be mechanically driven by a spring or driven pneumatically. In this example, the motor and light source are driven by a circuit board 126 which comprises a microcontroller and power transistors for running a set or programmable sequence of spin rates and optical detection steps. The circuit board may also be used to amplify and convert the signal from the optical sensor into a digital format. The instrument is powered by a voltage source 127. The voltage source 127 may originate from a battery pack or ac-dc adaptor.

FIGS. 13A-13C show an example of a configuration of a cartridge 131 intended for use in optically addressed or visual assays that require alignment of an assay output section 132 of the cartridge with a specific spatial analysis region 135, in accordance with one embodiment. The cartridge comprises an extended lower adaptor 133 that can securely connect with a motor 137 configured to power rotation of the cartridge. The adaptor 133 may comprise notches 134, wherein the notches are of the same diameter or width as an impinging mechanism 136. The impinging mechanism 136 is positioned such that movement of the mechanism toward the adaptor 133 causes interlock between the impinging mechanism 136 and a notch 134. This interlock causes the cartridge to stop such that the assay output section 132 and analysis region 135 are precisely aligned. The impinging mechanism may be located inside of the housing 138 to prevent external interference with the interlocking positioning method. Positioning of the impinging mechanism 136 may be achieved through action of an electrical motor or solenoid, or may be caused by a mechanical trigger such as the physical press of a user. Subsequent assay output sections 132 may be aligned with the analysis region 135 by coordinated rotation of the cartridge and movement of the impinging mechanism. Assay output sections 132 can contain pelleted particles for a sedimentation assay or control or blank particles or substances for assay calibration. The cartridge can be configured to have three or more assay output sections 132 and a corresponding number of notches 134 for alignment of the assay output sections 132 with the analysis region 135.

FIG. 14 is a diagram of an example of a set of process steps for practicing an embodiment of the disclosed for various embodiments of the cartridge described previously. Different embodiments may perform the illustrated steps in different orders, omit certain steps, and/or perform additional steps not shown in FIG. 14. Any of the methods described herein can be used with any of the cartridge or instrument embodiments described throughout.

Figure 13:
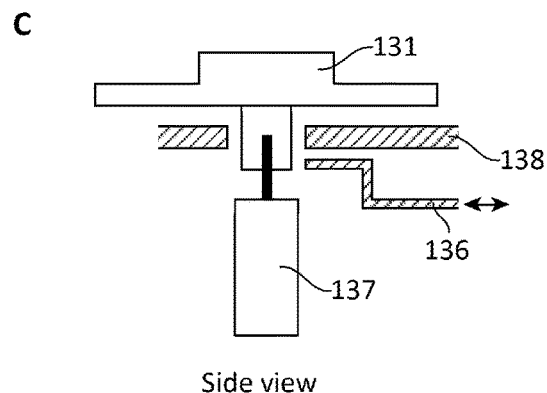
FIGS. 13A-13C show bottom (FIGS. 13A-13B) and side views (FIG. 13C) of a cartridge positioning by a notched hub adaptor and an impinging member, in accordance with one embodiment.

The cartridge receives 141 a solid or liquid sample. The cartridge can also receive 142 a liquid diluent or solid reagent from the user. As an alternative to receiving the liquid diluent from the user, the cartridge may initially contain the liquid diluent within a diluent container, which can be ruptured 147 following receipt of the sample from the user. The cartridge is then agitated 143 to homogenize the sample, as shown and described in the embodiments of FIGS. 6 and 7, allowing the sample to react with reagents in the sample inlet chamber if reagents are used. Duration of agitation can be from 5 seconds to 40 minutes and comprises rotating the cartridge in alternating clockwise and counter clockwise directions a plurality of times. Duration of agitation can also be 5 seconds to 40 minutes and comprise rotating the cartridge in one direction and then allowing the cartridge to come to a stop a plurality of times. Then, the cartridge is rotated 144 in one direction at a rotation rate that can be in the range 100-15000 RPM to sediment assay particles. The sample is then analyzed 145 by the user or by optical analysis through the light source 123 and optical sensor 124 integrated into the instrument such as shown in FIG. 12 or 13. In various embodiments, the cartridge is also aligned with an analysis region as shown in FIG. 13. Either the user or the instrument then records 146 the resulting measurement information.

FIG. 15 is a diagram of an example of a set of process steps for performing an embodiment of the disclosed from a user's perspective. The user adds 151 a solid or liquid sample to the cartridge. The user can also add 152 a liquid diluent (to aid in analysis of a concentrated liquid sample or solid sample) and/or solid reagents. The user then attaches 153 the cartridge to an instrument comprising a motor configured to rotate the cartridge. The instrument can also comprise analysis optics such as those illustrated in FIG. 12. The user may then initiate 154 the assay, resulting in the instrument automatically running the necessary spin and analysis steps on the cartridge. The instrument can be configured to display or output the data so that the user can read 155 the results of any assays performed.

FIG. 16 illustrates embodiments of methods for assisting the user when adding liquid samples or reagents to the central sample inlet cavity or sample inlet cavity of a cartridge.

FIGS. 16A-16D illustrate a structure having a sample inlet cavity 161 comprising a sample inlet hole 162 and two ridges 163 configured to restrict fluid from passing directly overhead of each ridge, in accordance with one embodiment. The structure illustrated simplifies filling the sample inlet cavity with liquid samples or reagents. The disclosed structure may be used with any of the cartridge embodiments described throughout. The structure is configured to allow venting of air from the sample inlet hole 162 while fluid 164 is input into the same sample inlet hole. Once fluid is in contact with all edges of the sample inlet hole 162 (i.e. the sample inlet hole is surrounded by fluid), fluid may cease to flow if no air escape hole is provided due to a buildup of air pressure. This buildup can prevent complete use of the space in the sample inlet cavity. In this embodiment, the two ridges 163 within the sample inlet cavity are configured to restrict fluid from passing directly overhead of each ridge structure within the sample inlet cavity and direct fluid to fill one side of the sample inlet cavity first and then the other as shown in FIG. 16B through 16D. The cartridge can also comprise features 163 that are depressions in the floor of the sample inlet cavity, rather than ridges. If capillary forces exceed a threshold force, fluid is prevented from entering the features 163. The restriction of fluid movement around the features 163 permits nearly complete filling of the sample inlet cavity before the sample inlet hole 162 is surrounded by fluid and air venting from the sample inlet hole is restricted. More than two ridges or depressions configured to restrict fluid from passing directly overhead can also be used so that buildup of air pressure is prevented from multiple angles around the sample inlet hole. A single ridge or depression within the sample inlet cavity can also be used to allow self-venting of the sample inlet cavity.

FIG. 17 illustrates an example of a sample inlet cavity 171 and agitation enhancement beads 173 used within the sample inlet cavity 171 to assist with sample agitation/homogenization, in accordance with one embodiment. Therefore, the beads 173 will aid in homogenizing liquid or solid-in-liquid samples similar to the tooth structures described in FIGS. 6 and 7. The enhancement beads 173 can also comprise dried or solid reagents. The enhancement beads can be placed in the sample inlet cavity during manufacturing or by the user through the sample inlet hole 172. The enhancement beads 173 can be used with any of the cartridge embodiments described throughout. A bead may comprise a solid core 174 plus a coating of reagent 175. The bead can also have a solid outer layer with a dissolvable reagent core that is exposed to the surface in a plurality of places. The bead may also comprise a solid object with notches filled with dissolvable reagent.

FIGS. 18A-18E illustrate a cartridge 181 for analyzing a defined amount of liquid or liquefied sample for multiple parameters using a single sample source, in accordance with one embodiment. In FIG. 18A, the cartridge 181 comprises a sample inlet cavity 183 comprising a sample inlet hole 182 in fluid communication with mixing chambers 185 by way of narrow passages or active valves 184. Each mixing chamber 185 can contain a stored solid or liquid reagent pellet 186 and be connected to a sedimentation tube 188 by way of another narrow passage or valve 187, wherein the valve 187 can be an active/passive valve. The sedimentation tubes 188 can contain density medium 189. The sample inlet cavity 183 can further be connected to overflow chambers 1810 by way of a narrow passage or active/passive valve 1811. Upon addition of liquid or liquefied sample 1812 and slow rotation of the cartridge (i.e. 100-2000 RPM), the sample forms an annulus within the sample inlet cavity as shown in FIG. 18B. Upon reaching a threshold rotation rate (i.e. 200-3000 RPM), a defined amount of fluid enters the mixing chambers and is prevented from flowing through the valve 187 due to configuration of the valves and capillary force or active valving as shown in FIG. 18C. Upon reaching a second threshold rate (i.e. 300-4000 RPM) as illustrated in FIG. 18D, or upon release of active valves as shown in FIG. 18D, the sample liquid remaining in the sample inlet cavity 183, as shown in a pre-fill state in FIG. 18C, passes through the valve 1811 into the overflow chambers 1811. Subsequent agitation of the cartridge can be used to aid in dissolving the reagent pellet 186 stored in the mixing chamber, forming an assay particle suspension 1813. Sandwich assay complexes may form in the mixing chamber. For example, the agitation can be through repeatedly alternating rotation in one direction and then in another direction. Upon rotation at an increased rate or agitation rate (i.e. 300-15000 RPM) shown in FIG. 18D, the particle suspension may flow through the valve 187 and be layered on top of the density medium 189 within the sedimentation tube 188. Maintaining the final spin rate for an interval of time (i.e. 30 seconds to 30 minutes) shown in FIG. 18E, results in the formation of pellets 1814 within the sedimentation tubes 188. Pellets 1814 may be analyzed to make measurements. The embodiment shown comprises three analysis chambers, but may include one or more analysis chambers. Depending on the number of analysis chambers, sizes of the mixing and overflow chamber and the diameter of the sample inlet cavity can vary.

Figure 19:
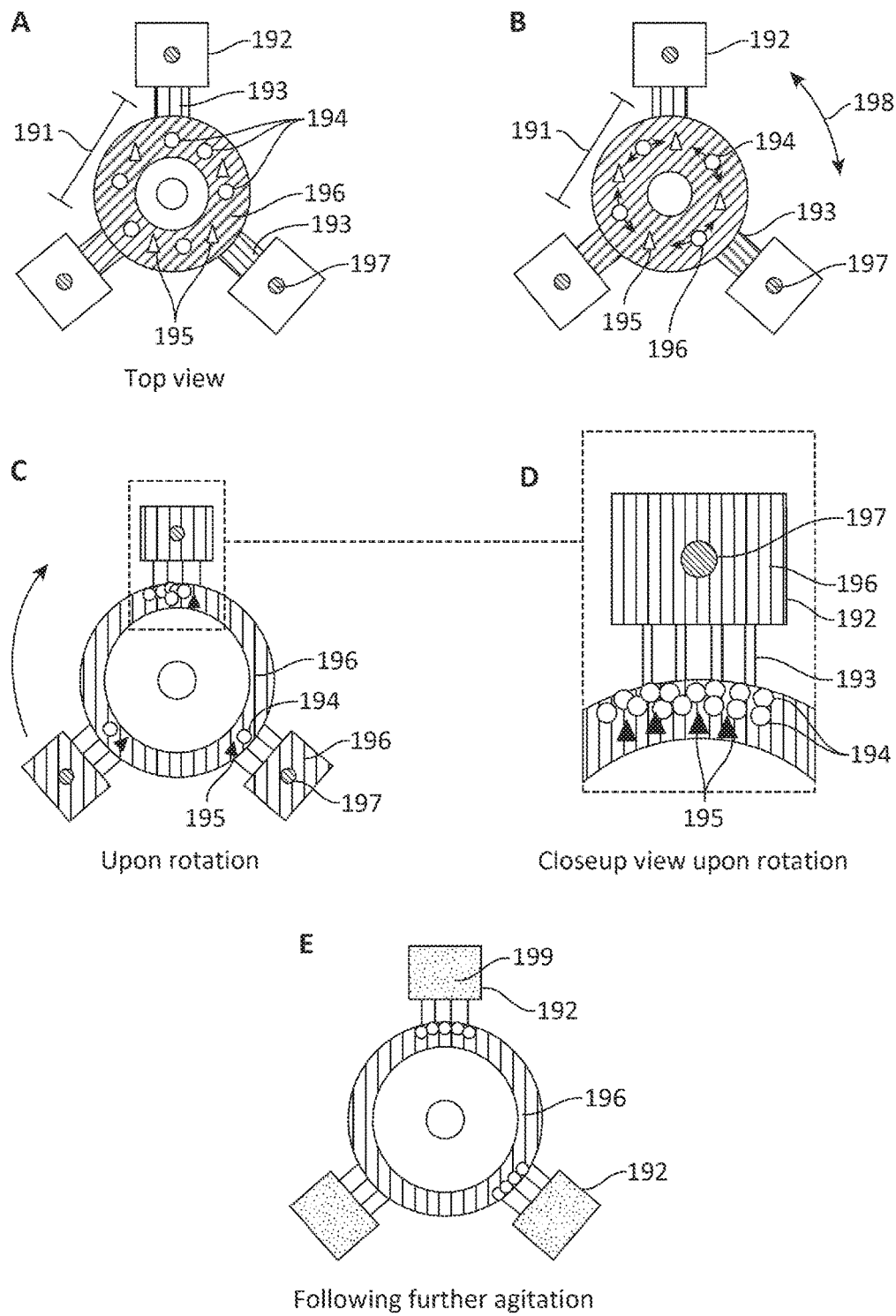
FIGS. 19A-19E show top views of a cartridge for filtering contaminant particles by small, dense filtration particles contained within the sample inlet cavity, in accordance with one embodiment.

FIGS. 19A-19E illustrate a technique for analyzing a sample that contains suspended particulate contaminants 195, in accordance with one embodiment. In FIG. 19A, cartridge comprises a sample inlet cavity 191 and the sample inlet cavity 191 is in fluid communication with analysis chambers 192 by way of narrow passages or a valve. In this embodiment multiple valves 193 are used to connect the sample inlet cavity 191 to the analysis chambers 192. An analysis chamber may contain a pellet of solid or liquid reagents 197. The sample inlet cavity is initially filled with a fluid sample 196, wherein the fluid sample 196 contains suspended particulate contaminants 195 and is mixed with filtering particles 194. The filtering particles 194 may also be suspended in the liquid. Upon agitation of the cartridge by repeatedly alternating rotation in one direction and then in another direction 198, as shown in FIG. 19B, the filtering particles 194 act as agitation enhancement beads and help to homogenize the sample. The cartridge may then be rotated at a threshold rate (i.e. 100-3000 RPM), driving fluid through the valves 193, as shown in the state upon rotation illustrated in FIG. 19C. If the filtering particles 194 are equal to or greater than a threshold width, wherein the threshold width is large enough such that the valves 193 are blocked, the filtering particles 194 can form a barrier, as shown in FIG. 19D. The barrier prevents contaminating particulates 195 from entering the analysis chamber. Sand particles may provide an inexpensive filtering particle source in various embodiments. Following the rotation, sample fluid 195 relatively uncontaminated with particulates fills the analysis chamber 192. Following further agitation of the cartridge by repeatedly alternating rotation in one direction and then in another direction, as shown in FIG. 19E, the reagent pellet 197 may dissolve, facilitating a desired chemical reaction, and thereby provide a reacted sample 199. This chemical reaction may be used to perform a sedimentation assay or may be used in another type of chemical assay. In some embodiments a sedimentation tube (not shown) may be configured radially outward from the analysis chamber 192. The embodiment shown comprises three analysis chambers, but may include one or more analysis chambers. Depending on the number of analysis chambers, sizes of the mixing and overflow chamber and the diameter of the inlet cavity can vary.

Figure 20:
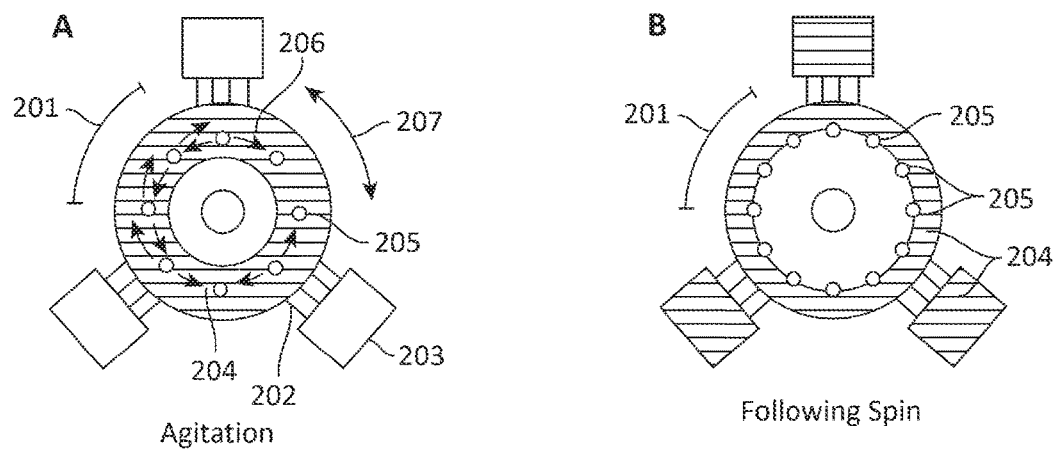
FIGS. 20A and 20B illustrate a technique using beads for sample agitation enhancement within a cartridge sample inlet cavity, in accordance with one embodiment.

FIGS. 20A and 20B illustrate a technique for providing agitation enhancement beads 205 without interfering with fluid flow or assay output based on unwanted sedimentation of these beads during centrifugation, in accordance with one embodiment. In FIG. 20A, cartridge comprises a sample inlet cavity 201 which is in fluid communication with analysis chambers 203 by way of narrow passages or a valve 202. In this example multiple valves 202 are used to connect the sample inlet cavity 201 to the analysis chambers 203. An analysis chamber may contain a pellet of solid or liquid reagents. The sample inlet cavity is initially filled with a fluid sample 204 which is mixed with agitation enhancement beads 205 that comprise a density less than density of the sample fluid. Upon agitation of the cartridge by repeatedly alternating rotation of the cartridge in one direction and then in another direction 207, the agitation enhancement beads 205 also move in alternating rotation and thus directions 206 responsive to the rotation of the cartridge in the fluid sample 204 and homogenize the sample. In FIG. 20B, the cartridge may then be rotated at a threshold rate (i.e. 100-3000 RPM) driving fluid through the valves 202 and into the analysis chambers 203. The agitation enhancement beads 205 float atop the remaining fluid 204 in the sample inlet cavity 201 and therefore do not interfere with fluid movement, nor enter the analysis chamber. The agitation enhancement beads can be made from low density polymers, wood particles, or glass microballoons. The material of the agitation enhancement beads can be used in a sedimentation assay or be used in another type of chemical assay. A sedimentation tube (not shown) may be configured radially outward from the analysis chamber 203. The embodiment shown comprises three analysis chambers, but may include one or more analysis chambers.

FIGS. 21A and 21B show a method for marking the top surface of liquid levels during sedimentation assays using low density particles 213, in accordance with one embodiment. In FIG. 21A, a sample fluid 212, mixed with assay particles 214 and low density particles 213, is initially contained in a narrow channel 211, also known as a sedimentation column or channel. Upon centrifugation or upon incubation, as shown in FIG. 21B, the assay particles form a defined pellet 215 at the bottom of the narrow channel 211 and the low density particles 213 form a layer at the interface between the sample fluid 212 and the air or other fluid atop the sample fluid 212. This layer of low density particles may be used to identify the amount of sample fluid contained in the column. For example, the low density particles 213 are dyed with a colored or fluorescent compound, assisting in the identification of or calibrating an assay for the amount of sample fluid. The fluid 212 may also comprise a reagent, and the low density particle layer 213 can assist in calibration for the amount of reagent used. A density medium may be included in the narrow channel. The density medium here can be used in a similar manner as used in the sedimentation tube described throughout herein. In addition, the narrow channel can be used in a similar manner as the sedimentation tube described throughout herein. In some embodiments, the low density particles 213 can comprise particulates resulting from manufacturing or production of the cartridge.

Figure 22:
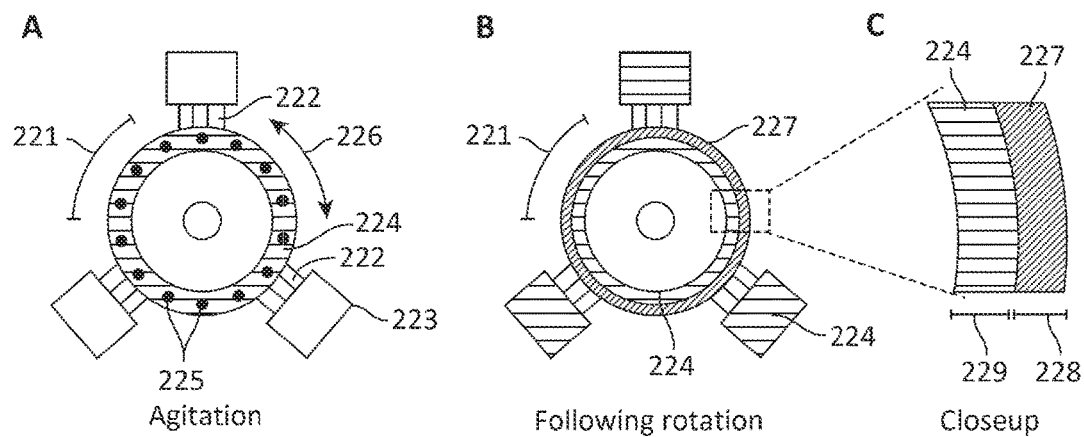
FIGS. 22A-22C show the chambers within a cartridge used for analyzing samples comprising a suspension with a fluid component containing a substantial volumetric fraction of solid, in accordance with one embodiment.
Figure 23:
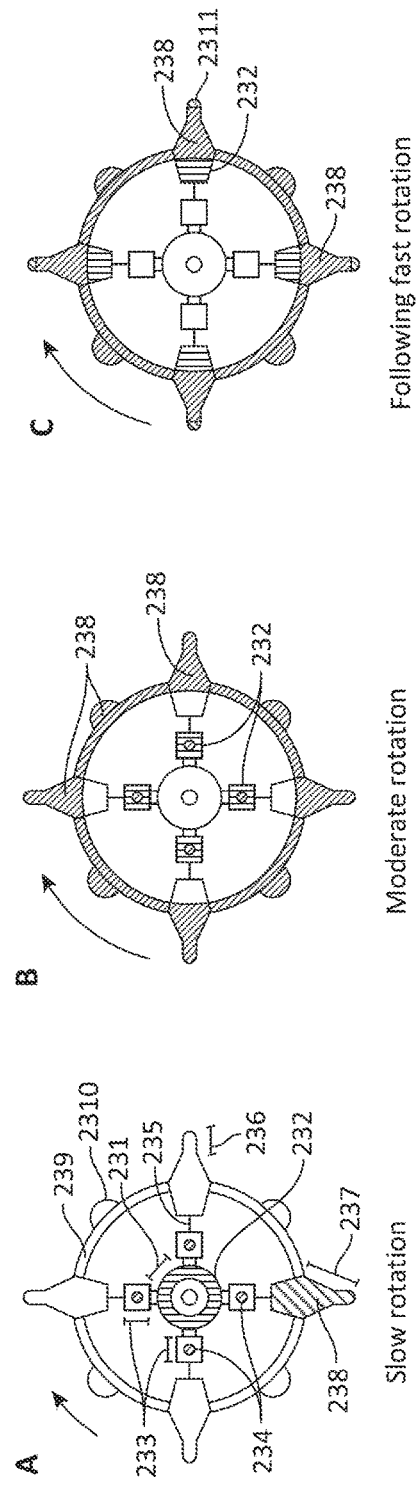
FIGS. 23A-23C depict fluidic cavities within a cartridge intended for simultaneous distribution of density medium and sample, each from a single initial location, in accordance with one embodiment
Figure 24:
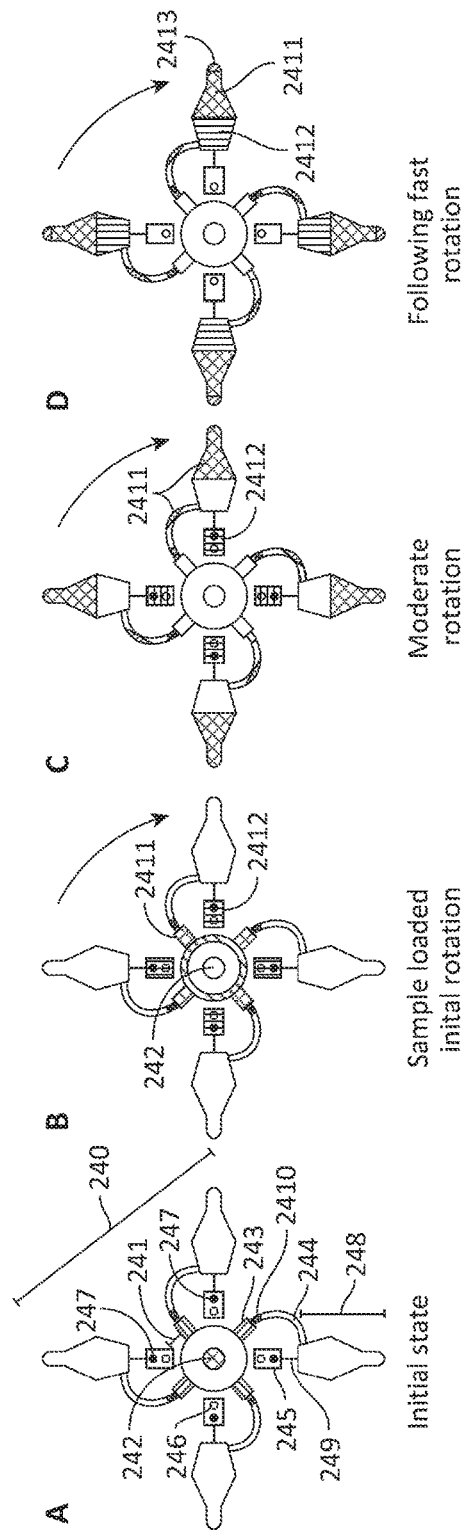
FIGS. 24A-24D depict fluidic cavities within a cartridge intended for distribution of density medium from a single initial location and simultaneous processing of individual samples, in accordance with one embodiment.

FIGS. 22A-22C depict chambers within a cartridge used for analyzing samples comprising a suspension with a fluid component 224 containing a substantial volumetric fraction (e.g. >1%) of solid particles 225, in accordance with one embodiment. As shown in FIG. 22A, the suspension is initially located in a sample inlet cavity 221 where the suspension may be agitated by rotation in one direction and then in another direction 226. The sample is then driven through the narrow channels or valves 222 into the analysis chambers 223 during rotation in one direction at a rotation rate (i.e. 100-15000 RPM) as shown in FIG. 22B. The solid particles 225 can be prevented from entering the analysis chambers 223 through the filtration process previously described in FIG. 19D, enabling analysis of the fluid component 224 along with any dissolved substances and not the solid particles 225. Following rotation for an interval of time (i.e. 30 seconds to 30 minutes), the solid particles form a compacted region 227 at the periphery of the sample inlet cavity 221 (shown in FIG. 22C). The initial amount and bulk composition of the sample can be estimated based on thickness 228 of the compacted region 227 and thickness 229 of the remaining fluid layer in the sample inlet cavity. The estimate can be made based on a known volume of the fluid component 224 and known dimensions of the sample inlet cavity 221. This estimate can be more accurate if the solid particles 225 have a known packing density following centrifugation of whole blood, semen, soil in water suspensions, and other commonly sedimented samples. The embodiment described in FIG. 22 may be particularly useful for measuring soluble components of soil samples, where the larger particulates in soil act as filter particles, as described in conjunction with FIG. 19, and estimation of the ratio of soil particles to diluting water is necessary for accurate analysis. A sedimentation tube (not shown) may be configured radially outward from the analysis chamber 223. The embodiment shown comprises three analysis chambers, but may include one or more analysis chambers. Depending on the number of analysis chambers, sizes of the mixing and overflow chamber and the diameter of the inlet cavity can vary.

The embodiments of cartridges described in FIGS. 23-27 are designed to successfully store liquid density medium and dry reagents for an extended interval of time. This can be achieved by sealing any dried reagents from water vapor and by storing liquid reagents such as density medium in liquid and vapor tight pouches. Thus, the embodiments described in FIGS. 23-27 are configured to be able to seal the stored liquid density medium and dry reagents in liquid and vapor tight pouches for an extended interval of time.

FIGS. 23A-23C depict fluidic cavities within a cartridge configured to simultaneously distribute density medium 238 and sample 232, in accordance with one embodiment. The density medium 238 is initially positioned at a single location within the cartridge. The cartridge comprises a sample inlet cavity 231 in fluid communication with mixing chambers 233 and the cartridge can have reagent pellets 234. The mixing chambers 233 are further in fluid communication with sedimentation tubes 237 by way of narrow channels or valves 235. The valves 235 may comprise vapor barriers. The sedimentation tubes 237 are connected to one another by circumferential channels 239. The cartridge may further comprise particle trap features 2310 in fluid communication with the circumferential channels 239. In this example, the density medium 238 is initially contained in one of the sedimentation tubes 237, and may be further contained in a liquid and vapor impermeable pouch that can be punctured by a user of the cartridge. Upon rotation of the cartridge at a moderate rotation rate in the range of 100-3000 RPM, the sample 232 becomes equally distributed in the one or more mixing chambers 233. The sample 232 may rehydrate and begin to dissolve the reagent pellets 234. Even distribution of sample can be aided by overflow chambers (not shown) as described in conjunction with FIG. 18. The moderate rotation of the cartridge also causes the density medium 238 to become equally distributed in the one or more sedimentation tubes 237 through the circumferential channels 239. Following a rotation of the cartridge at a rotation rate faster than the moderate rotation rate (i.e. 200-15000 RPM), the sample fluid mixed with reagents exits the mixing chambers and is layered on top of a density medium 238. The circumferential channels are configured to create high flow resistance to maintain even distribution of density medium as the sample 232 is layered on the density medium, which creates brief imbalances in fluid height among the narrow channels 236. Faster rotation for an interval of time (i.e. 30 seconds to 30 minutes) causes assay particles initially contained in the reagent pellets to sediment out of the sample, through the density medium, and form compact pellets 2311 at an outer edge of the narrow channels. The particle trap features 2310 are configured to prevent sedimentation particles from crossing over between sedimentation tubes 237 and interfering with separate analysis of each pellet 2311. The embodiment shown comprises four analysis chambers, but may include one or more analysis chambers. Depending on the number of analysis chambers, sizes of the mixing and overflow chamber and the diameter of the sample inlet cavity can vary.

Figure 18:
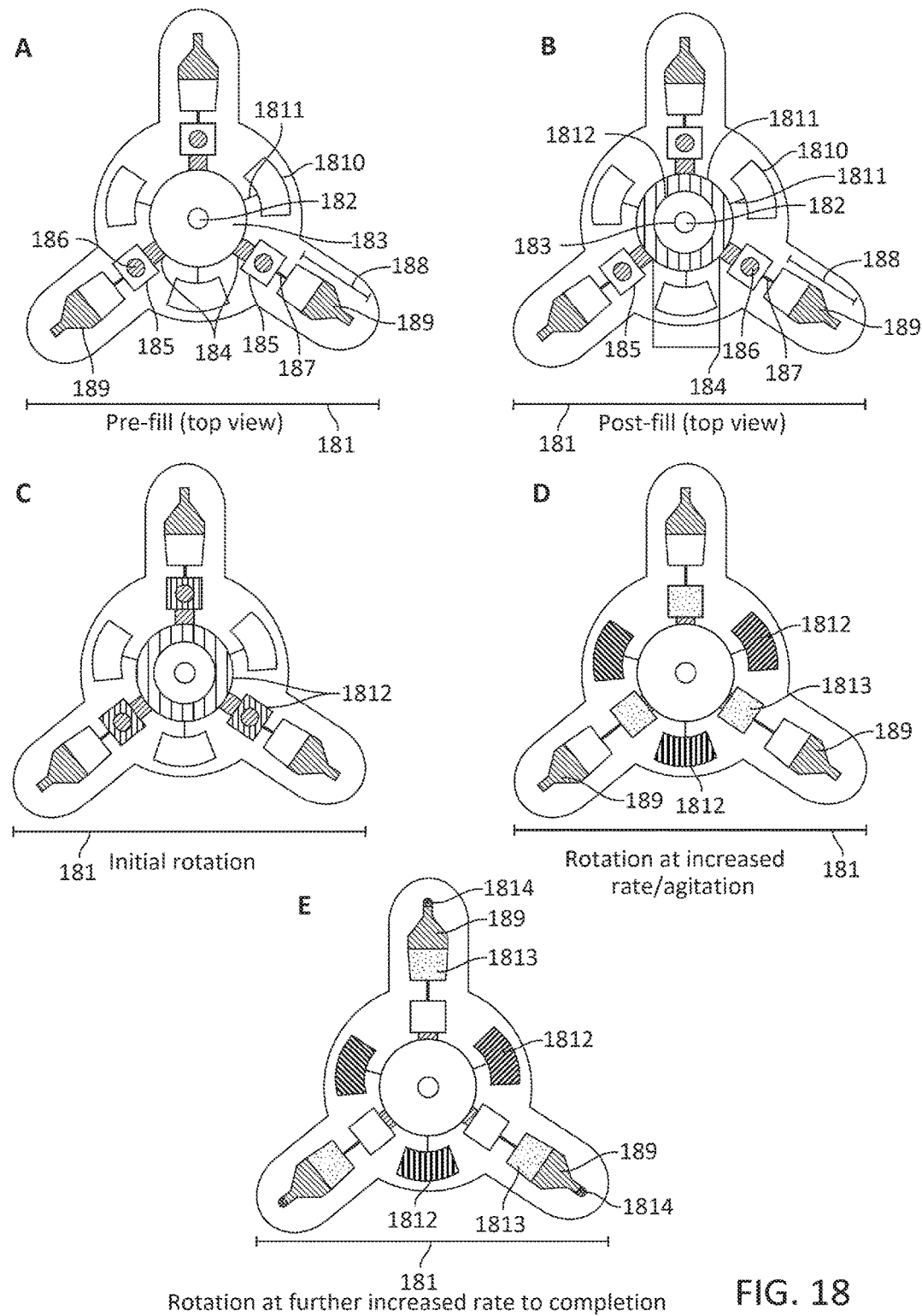
FIGS. 18A-18E show top views of a cartridge for analyzing multiple parameters using a single liquid sample, in accordance with one embodiment.

FIGS. 24A-24D illustrate a cartridge 240 having fluidic cavities that are configured for distribution of density medium 2411 from a single initial location, such as the sample inlet cavity, and simultaneous processing of individual samples 2412, in accordance with one embodiment. The cartridge contains a central medium distribution or sample inlet cavity 241 in fluid communication with medium metering chambers 243. The medium metering chambers 243 are in fluid communication with medium distribution channels 244 by way of a constriction or valve 2410. The medium distribution channels 244 connect with sedimentation tubes 248. For example, the medium distribution channels 244 connect with the inner edge (towards center) of the sedimentation tubes 248. For example, the inner edge of a sedimentation tube 248 refers to a proximal end of the sedimentation tube 248 relative to the sample inlet cavity 241. In this example, the outer edge of the sedimentation tube 248 refers to a distal end of the sedimentation tube 248 relative to the sample inlet cavity 241. Each sedimentation tube is connected to an individual sample mixing cavity 245 by way of a narrow constriction or valve 249. Each sample mixing cavity 245 may contain a reagent pellet 247 and be user accessible by way of a sample inlet hole 246. To initiate the assay (FIG. 24A), the user may input individual samples into the sample mixing cavities 245 by way of the sample inlet holes 246, and rupture the density medium container pouch 242 which may initially be liquid and vapor impermeable. Upon a slow rotation in a range of 100-3000 RPM as shown in FIG. 24B, density medium 2411 escapes from the density medium container pouch 242 and becomes distributed among the medium metering chambers. The distribution process can be aided with the use of overflow chambers as depicted in FIG. 18 to assist in even distribution among the medium metering chambers 243. Upon moderate rotation (i.e. 200-4000 RPM) shown in FIG. 24C, density medium 2411 may pass through the constriction or valve 2410 and flow through the medium distribution channels 244 into the sedimentation tubes 248. Upon fast rotation (i.e. 300-15000 RPM) shown in FIG. 24D, sample containing dissolved reagents from the reagent pellet 247 passes through the valve 249 and becomes layered on the density medium 2411 within the sedimentation tubes 248. Continued fast rotation for an interval of time in the range of 30 seconds to 30 minutes causes assay particles contained in the sample to sediment through the density medium 2411 and form a compact pellet 2413 on the periphery of the sedimentation tubes where the compact pellet 2413 can be analyzed.

Figure 25:
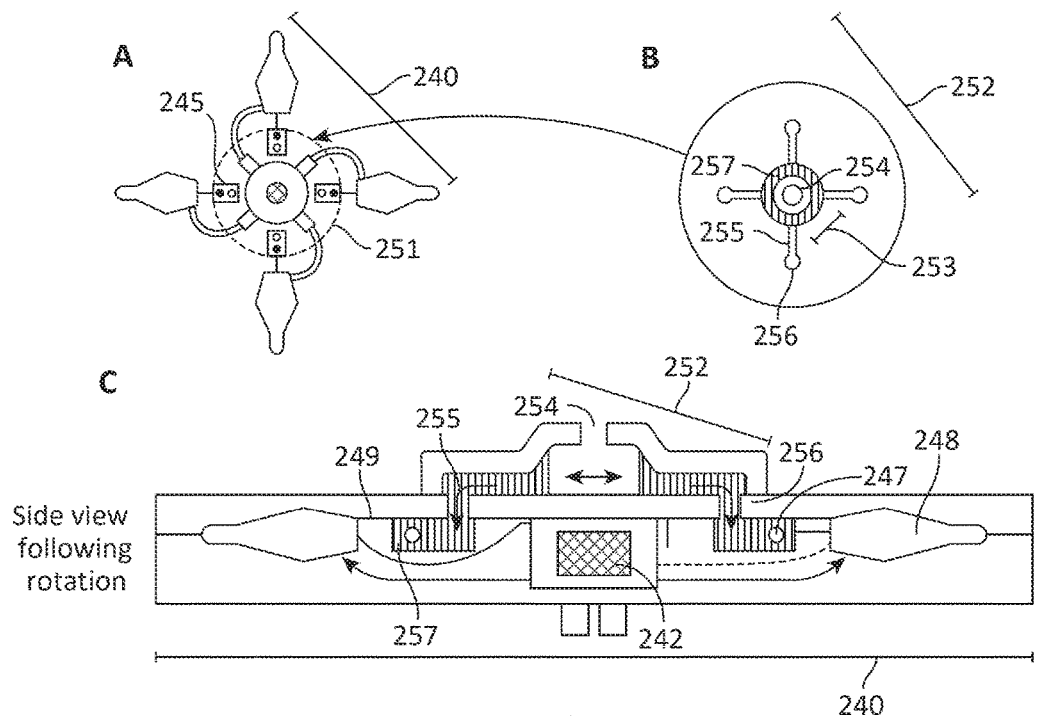
FIGS. 25A-25C depict an extension of the cartridge described in FIGS. 24A-24D allowing simultaneous distribution of both sample and density medium from respective central initial locations, in accordance with one embodiment.
Figure 26:
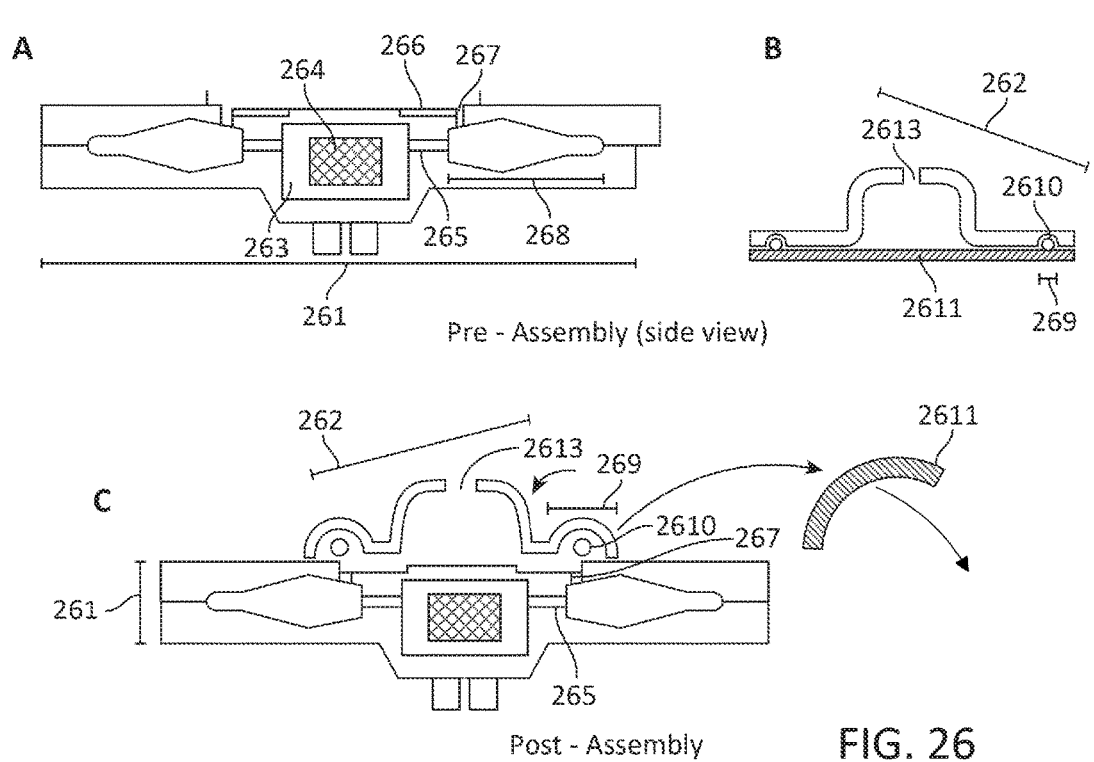
FIGS. 26A-26C depict a cartridge and extension which when combined allows simultaneous distribution of density medium and sample, in accordance with one embodiment.
Figure 27:
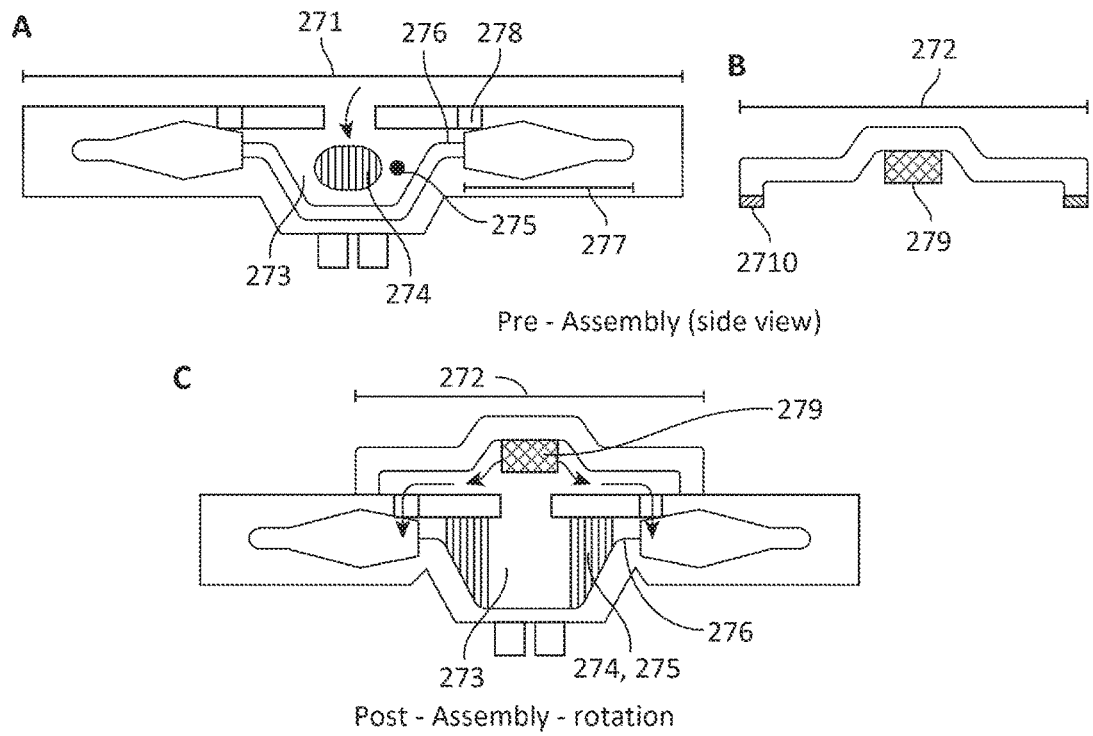
FIGS. 27A-27C depict a cartridge and extension which when combined allows simultaneous distribution of density medium and sample, in accordance with one embodiment.

FIGS. 25A-25C illustrate an extension piece 252 of the cartridge 240 described in FIGS. 24A-24D which may allow simultaneous distribution of both sample and density medium from respective central initial locations, in accordance with one embodiment. The cartridge has a marked surface, illustrated as a dotted line in FIG. 25A, allowing for the extension piece 252 to attach to the cartridge 240 in a defined location 251. When the extension piece 252 is attached to the cartridge 240 by methods which may include use of pressure sensitive adhesives, glues, or ultrasonic welding, depressions in the extension become enclosed fluid-tight cavities and channels. The resulting combined cartridge has a sample inlet cavity 253 with a sample inlet hole 254. The sample inlet cavity 253 is in fluid communication with metering channels 255. A distal end of the metering channels 255 comprises cavities 256. The cavities 256 line up with user accessible sample inlet holes 246 in the base of the cartridge 240. During rotation, the metering channels 255 can define amount of sample 257 which is evenly distributed among the mixing chambers 245. Even distribution can be aided with the use of overflow chambers as described in FIG. 18. The configuration of channels and cavities described here may allow distribution of density medium to the sedimentation tubes 248 as described in FIG. 24 followed by layering of sample 257 on top of the density medium 2411 without individual dispensing of sample into the mixing cavities 245 by the user. The extension 252 and cartridge 240 may be pre-assembled with an adhesive foil covering the sample inlet hole 254 to protect the reagent pellets 247 from water vapor. Alternately, the extension 252 and cartridge 240 can be assembled by the user using pressure sensitive adhesive or other suitable adhering technique, and the lower cartridge through user accessible sample inlet holes 246 covered with peel-able seals to protect the reagent pellets 247 from water vapor. The embodiments of cartridges shown in FIGS. 24 and 25 comprise four analysis chambers, but may include one or more analysis chambers. Depending on the number of analysis chambers, sizes of the mixing and overflow chamber and the diameter of the inlet cavity can vary.

FIGS. 26A-26C illustrate a cartridge 261 and extension 262 which when combined allow simultaneous distribution of density medium 264 and sample, in accordance with one embodiment. The cartridge may contain density medium 264 in a medium distribution cavity 263. The density medium 264 may be contained in a vapor and liquid tight pouch for long term storage. The medium distribution cavity 263 is in fluid communication with sedimentation tubes 268 by way of valve gated volume defining valves 265 which meters defined amounts of density medium 264 into each sedimentation tube upon rotation at a specified rate (i.e. 200-3000 RPM). The extension 262 shown in FIG. 26B contains a sample inlet cavity with a sample inlet hole 2613. The extension 262 further comprises reagent holding cavities 269 containing dry reagent or reagent pellets 2610. The reagent pellets 2610 are protected with a peel-able seal 2611 which initially covers the bottom of the extension 262. The peel-able seal 2611 can be removed by the user and discarded, and the extension 262 can be sealed to the cartridge 261 with adhesive, that can be pressure sensitive. This assembly creates sample metering channels 266 from grooves in the upper surface of the cartridge 261. When a liquid sample or solid in liquid sample is added to the cavities created by the extension 262 and the cartridge is rotated, the sample is first metered in equal aliquots into the metering channels 266 and reagent holding cavities 269. When sample enters the reagent holding cavities 269, the reagents 2610 are re-hydrated and react with the sample. When rotation reaches a sufficient rotation rate (i.e. 300-4000 RPM), the sample is driven through the narrow sample transfer valves 267 into the sedimentation tube 268. The sample will then form a layer on top of density medium 264 which will have previously been metered into the sedimentation tube 268.

FIGS. 27A-27C illustrate a cartridge 271 and extension 272 which when combined allows simultaneous distribution of density medium 279 and sample 274, in accordance with one embodiment. The lower cartridge may receive liquid or solid-in-liquid sample 274 into sample inlet cavity 273. The sample inlet cavity 273 may be in fluid communication with sedimentation tubes and narrow channels 277 by way of sample metering channels 276. Either the sample inlet cavity or sample metering channels may contain reagent pellets 275. The extension 272 may contain density medium 279 in an attached liquid and vapor tight pouch. The sample inlet hole and medium transfer holes 278 may be covered by a water-vapor tight peel-able seal (not shown). The user may remove any peel-able seals and attach the extension 272 to the cartridge 271 using attached pressure sensitive adhesive 2710 following dispensing of sample 274 into the sample inlet cavity 273. Rotation of the cartridge at a moderate rate (i.e. 100-3000 RPM) may allow even distribution of medium 279 by medium metering channels 276. Subsequent rotation of the cartridge at a faster rate (i.e. 200-4000 RPM) may cause sample 274 to be evenly distributed in the sample metering channels 276 and to be layered on top of the density medium 279 in the sedimentation tubes and narrow channels 277.

Figure 28:
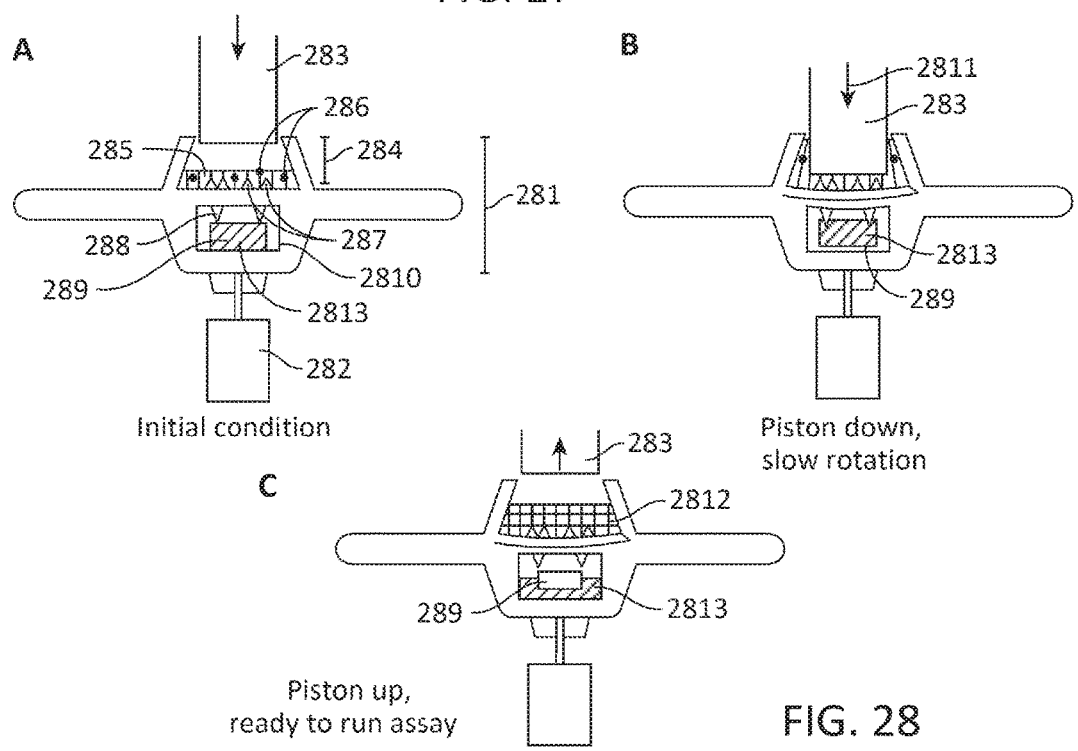
FIGS. 28A-28C depict a cartridge intended for processing and analysis of samples comprising solids or solid chunks suspended in a liquid, in accordance with one embodiment.

FIGS. 28A-28C illustrate a cartridge 281 that can be used to process and analyze samples comprising solids or solid chunks 286 suspended in a liquid 285, in accordance with one embodiment. Samples appropriate for this embodiment of the invention include but are not limited to food, soil, stool, and environmental samples. FIG. 28A shows cartridge 281 comprising a sample inlet cavity 284 and medium distribution cavity 2810. The medium distribution cavity 2810 contains a vapor and liquid impermeable medium pouch 289 filled with density medium 2813. The sample inlet cavity 284 can be lined with tooth like projections or ridges 287 configured to disrupt the solid chunks 286. The medium distribution cavity 2810 may have sharp tooth like projections 288 on its top or bottom surface facing the pouch containing density medium 2813. The cartridge can be mounted on a motor 282 which may be part of an analysis instrument. A piston 283 comprising a cross-section smaller than the cross-section of the sample inlet cavity 284 is aligned with the center of the cartridge. As shown in FIG. 28B, in order to crush chunks of solid 286 suspended in the sample liquid 285 into smaller solid chunks 286, the piston 283 is lowered into the sample inlet cavity 284 and a downward force 2811 is applied by the piston 283. The force 2811 causes the wall between the sample inlet cavity 284 and the medium distribution cavity 2810 to flex, resulting in tooth like projections 288 puncturing the medium pouch 289. The piston 283 may then be refracted slightly, as shown in FIG. 28C, leaving a small gap between the piston surface and surface of the sample inlet cavity 284. In one embodiment, the piston 283 can be left in place. Slow rotation (i.e. 20-1000 RPM) of the cartridge in this configuration creates fluid shear stress in the narrow band of liquid 285 trapped between the piston 283 and sample inlet cavity 284. This configuration during slow rotation also forces solid chunks 286 against the ridge or tooth structures 287, breaking the chunks 286 up into smaller chunks. When the sample has been crushed into a homogeneous suspension 2812 the piston 283 can be removed either by the user or automatically by the instrument. Upon rotation of the disk at a faster rate (i.e. 200-3000 RPM) the homogenized sample 2812 and the density medium 2813 can be distributed to analysis chambers and/or sedimentation tubes as described in previous examples.

The foregoing description and figures provide only some specific examples of different embodiments that can be incorporated into the invention. Other embodiments are also possible, including some with more, fewer, or different components than those provided and it will be appreciated that, although specific embodiments of the invention have been described herein these are intended for purposes of illustration. Various modifications may be made without deviating from the spirit and scope of the invention.

What is claimed is:

1. An apparatus comprising:
a cartridge having a center of rotation and configured to be rotated to cause sedimentation of particles or cells suspended in a sample, the cartridge comprising:
a receiving cavity configured to hold the sample, the receiving cavity having a sample entry hole configured to allow entry of the sample into the receiving cavity, wherein the receiving cavity is centered on the center of rotation of the cartridge;
a second cavity located farther from the center of rotation of the cartridge relative to a location of the receiving cavity, wherein the second cavity further comprises at least one wall, wherein the at least one wall is configured at an angle away from and relative to a radial line, the radial line projected away from the center of rotation of the cartridge and crossing the at least one wall, wherein a distal end of the second cavity from the center of rotation of the cartridge tapers to a smaller cross section than a cross section of the second cavity between a proximal end and the distal end of the second cavity; and
a passage connecting the receiving cavity and the second cavity, the passage having a cross-sectional area that is smaller than a cross-sectional area of the receiving cavity,
wherein the cartridge is configured to transfer the sample from the receiving cavity to the second cavity during rotation of the cartridge for sedimentation of the particles or cells.

2. The apparatus of claim 1 wherein the cartridge is configured for conducting a sandwich assay method comprising:
generating complexes on a plurality of the particles in the sample, wherein a complex comprises a capture agent, a target analyte, and a labeling agent;
transporting the plurality of particles including the complexes through a density media, wherein the density media has a density lower than a density of the particles and higher than a density of the sample, and wherein the transporting occurs, at least in part, by sedimentation; and
detecting a signal from the labeling agents of the complexes.

3. The apparatus of claim 1, wherein the second cavity further comprises a narrow channel of reduced cross section, the reduced cross section being smaller than a cross section of the second cavity between a proximal end and a distal end of the second cavity from the center of rotation of the cartridge, the narrow channel of reduced cross section coupled to the distal end of the second cavity.

4. The apparatus of claim 3, wherein the channel of reduced cross section is configured to retain density media by capillary forces following cartridge rotation to move density media into the second cavity.

5. The apparatus of claim 1, wherein the second cavity is configured to store one or more density media.

6. The apparatus of claim 1, wherein the cartridge further comprises a plurality of second cavities.

7. The apparatus of claim 6, wherein the receiving cavity is configured to direct a portion of the sample initially in the receiving cavity into the plurality of second cavities during rotation, and wherein the cartridge further comprises one or more overflow cavities configured to receive remaining sample from the receiving cavity during rotation of the cartridge.

8. The apparatus of claim 6, further comprising an extension containing density media attachable to the cartridge, wherein the extension is configured to distribute density media to the plurality of second cavities during rotation through enclosed channels formed by attachment of the extension to the cartridge.

9. The apparatus of claim 6, wherein the cartridge further comprises a distribution cavity configured to hold density media, and wherein the cartridge is configured to distribute density media to each second cavity of the plurality of second cavities during rotation.

10. The apparatus of claim 9, wherein the distribution cavity configured to hold density media is located below the receiving cavity.

11. The apparatus of claim 1, wherein the cartridge further comprises one or more pouches configured to hold density media and resist evaporation of the density media, and wherein the pouches may be ruptured to release the density media.

12. The apparatus of claim 1, wherein the cartridge further comprises one or more third cavities closer to the center of rotation of the cartridge than the second cavity and farther from the center of rotation of the cartridge than the receiving cavity, wherein the cartridge is configured to transfer a portion of the sample from the receiving cavity to the one or more third cavities during rotation of the cartridge.

13. The apparatus of claim 12, wherein each of the one or more third cavities is configured to hold a solid reagent configured to dissolve in the sample, and wherein the solid reagent is configured to aid in analyzing the sample.

14. The apparatus of claim 1, wherein the receiving cavity is configured to hold a sample comprising solid particles in contact with a liquid component, wherein the liquid component is configured to dissolve elements associated with the solid particles, and wherein the second cavity contains reagents configured to aid in analyzing the liquid component of the sample and elements dissolved in the liquid component.

15. The apparatus of claim 14, wherein the passage connecting the receiving cavity to the second cavity is configured to retain a portion of the solid particles within the receiving cavity and allow a portion of the liquid component to enter the second cavity during rotation of the cartridge.

16. The apparatus of claim 14, wherein the passage connecting the receiving cavity to the second cavity is smaller in at least one dimension than the diameter of at least one solid particle from a portion of the solid particles.

17. The apparatus of claim 15, further comprising a system for measurement of the portion of solid particles retained in the receiving cavity to estimate a quantity of solid particles in the sample.

18. The apparatus of claim 14, wherein the solid particles comprise soil particles.

19. The apparatus of claim 1, wherein the apparatus is configured to aid in measuring a quantity of solid particles suspended in the sample by sedimenting the solid particles into a pellet within the second cavity during rotation of the cartridge.

20. The apparatus of claim 1, wherein the sample comprises solid particles in contact with a liquid component, wherein the liquid component is semen and the solid particles are sperm cells.

21. The apparatus of claim 1, wherein the receiving cavity further comprises one or more projections from a bottom of the receiving cavity, wherein the projections are configured to aid in homogenization of the sample.

22. The apparatus of claim 21, wherein a height of the one or more projections is less than a height of the receiving cavity, and wherein the projections are configured to prevent liquid from encircling the sample entry hole during transfer of liquid to the receiving cavity.

23. The apparatus of claim 1, wherein the receiving cavity further comprises objects, wherein a density of the objects is higher or lower than a density of liquid in the sample, and wherein the objects are configured to aid in homogenization of the liquid.

24. The apparatus of claim 23, wherein the objects further comprise reagents configured to aid in analysis of the sample.

25. The apparatus of claim 1, further comprising an instrument, wherein the instrument includes a motor configured to rotate the cartridge.

26. The apparatus of claim 25, wherein the motor further comprises a shaft, and wherein the cartridge further comprises a mate configured to couple the cartridge to the shaft.

* * * * *